US011771880B2

(12) United States Patent
Skinner et al.

(10) Patent No.: US 11,771,880 B2
(45) Date of Patent: Oct. 3, 2023

(54) IMPLANTABLE VENOUS ACCESS PORT WITH REMOTE PHYSIOLOGICAL MONITORING CAPABILITIES

(71) Applicant: NXgenPort, L.L.C., Saint Paul, MN (US)

(72) Inventors: Cathy Skinner, Saint Paul, MN (US); Rosanne Welcher, Ventura, CA (US); Mohamed Ali, Chicago, IL (US); Aenor Sawyer, Oakland, CA (US)

(73) Assignee: NXGENPORT, LLC, Saint Paul, MN (US)

( * ) Notice: Subject to any disclaimer, the term of this patent is extended or adjusted under 35 U.S.C. 154(b) by 593 days.

(21) Appl. No.: 16/932,503

(22) Filed: Jul. 17, 2020

(65) Prior Publication Data

US 2021/0016074 A1 Jan. 21, 2021

Related U.S. Application Data

(60) Provisional application No. 62/875,182, filed on Jul. 17, 2019.

(51) Int. Cl.
*A61M 39/02* (2006.01)

(52) U.S. Cl.
CPC . *A61M 39/0208* (2013.01); *A61M 2039/0205* (2013.01); *A61M 2205/3303* (2013.01);
(Continued)

(58) Field of Classification Search
CPC ...... A61M 39/0208; A61M 2039/0205; A61M 2205/3303; A61M 2205/3306;
(Continued)

(56) References Cited

U.S. PATENT DOCUMENTS

| 5,590,660 A | 1/1997 | MacAulary et al. |
| 5,951,521 A | 9/1999 | Mastrototaro |

(Continued)

FOREIGN PATENT DOCUMENTS

| CA | 2715628 A1 | 8/2009 |
| DE | 102011078711 A1 | 1/2013 |

(Continued)

OTHER PUBLICATIONS

Schnell, Reduction of Lipofuscin—like Autofluorescence in Fluorescently Labeled Tissue, 1999, J Histochem Cytochem. (Year: 1999).*

(Continued)

*Primary Examiner* — Amber R Stiles
*Assistant Examiner* — Nelson Louis Alvarado, Jr.
(74) *Attorney, Agent, or Firm* — Kunzler Bean & Adamson; Tom Briscoe

(57) ABSTRACT

An apparatus for an implantable venous access port with remote physiological monitoring capabilities is disclosed. A system and method also perform the functions of the apparatus. In one embodiment the apparatus includes a chemotherapy access port, a plurality of sensors integrated with the chemotherapy access port, where the plurality of sensors determine one or more chemotherapy-related physiological indicators and the one or more physiological indicators include at least parameters selected from red blood cell count, white blood cell count, platelets, and/or ejection fraction. The apparatus includes a communications module integrated with the chemotherapy access port, where the communications module is configured to communicate the one or more chemotherapy-related physiological indicators to a computing device.

20 Claims, 13 Drawing Sheets

(52) U.S. Cl.
CPC ............... *A61M 2205/3306* (2013.01); *A61M 2205/3553* (2013.01); *A61M 2210/12* (2013.01); *A61M 2230/04* (2013.01); *A61M 2230/20* (2013.01)

(58) Field of Classification Search
CPC ...... A61M 2205/3553; A61M 2210/12; A61M 2230/04; A61M 2230/20; A61M 2205/3561; A61M 2205/52; A61M 2205/8206; A61M 2205/8243; A61M 2205/8293; A61B 5/14503; A61B 5/14546; A61B 5/1459
See application file for complete search history.

(56) References Cited

U.S. PATENT DOCUMENTS

| | | | |
|---|---|---|---|
| 5,995,860 | A | 11/1999 | Sun et al. |
| 6,402,689 | B1 | 6/2002 | Scarantino |
| 6,659,959 | B2 | 12/2003 | Brockway et al. |
| 6,662,048 | B2 | 12/2003 | Balczewski et al. |
| 7,070,591 | B2 | 7/2006 | Adams et al. |
| 7,429,245 | B2 | 9/2008 | Whitaker et al. |
| 7,491,232 | B2 | 2/2009 | Boldue et al. |
| 7,515,953 | B2 | 4/2009 | Madar et al. |
| 7,595,723 | B2 | 9/2009 | Heitzmann et al. |
| 7,613,491 | B2 | 11/2009 | Boock et al. |
| 7,616,992 | B2 | 11/2009 | Dennis et al. |
| 7,727,181 | B2 | 6/2010 | Rush |
| 7,768,408 | B2 | 8/2010 | Reggiardo et al. |
| 7,783,333 | B2 | 8/2010 | Brister et al. |
| 8,025,639 | B2 | 9/2011 | Powers et al. |
| 8,073,517 | B1 | 12/2011 | Burchman |
| 8,251,904 | B2 | 8/2012 | Zivitz et al. |
| 8,257,325 | B2 | 9/2012 | Schweikert et al. |
| 8,265,556 | B2 | 9/2012 | Tekin et al. |
| 8,285,367 | B2 * | 10/2012 | Hyde ................. A61B 5/14546 600/476 |
| 8,364,229 | B2 | 1/2013 | Simpson et al. |
| 8,467,972 | B2 | 6/2013 | Rush |
| 8,547,248 | B2 | 10/2013 | Zdeblick |
| 8,920,343 | B2 | 12/2014 | Sabatino |
| 8,932,271 | B2 | 1/2015 | Hamatake et al. |
| 9,079,004 | B2 | 7/2015 | Wiley et al. |
| 9,135,402 | B2 | 9/2015 | Mensinger et al. |
| 9,138,536 | B2 | 9/2015 | Stefani et al. |
| 9,220,917 | B2 | 12/2015 | Boyden et al. |
| 9,265,912 | B2 | 2/2016 | Draper et al. |
| 9,474,888 | B2 | 10/2016 | Wiley et al. |
| 9,682,186 | B2 | 6/2017 | Powers et al. |
| 9,707,339 | B2 | 7/2017 | Chartrand et al. |
| 9,763,609 | B2 | 9/2017 | Simpson et al. |
| 9,833,603 | B2 | 12/2017 | Nardone et al. |
| 9,839,395 | B2 | 12/2017 | Shariati et al. |
| 10,016,151 | B2 | 7/2018 | Tangrea |
| 2003/0060695 | A1 | 3/2003 | Connelly |
| 2003/0177031 | A1 | 9/2003 | Malek |
| 2004/0044301 | A1 | 3/2004 | Levin |
| 2004/0054352 | A1 | 3/2004 | Adams et al. |
| 2004/0164961 | A1 | 8/2004 | Bal et al. |
| 2005/0261561 | A1 | 11/2005 | Jones et al. |
| 2006/0184141 | A1 | 8/2006 | Smith et al. |
| 2007/0049806 | A1 | 3/2007 | Adams |
| 2007/0112274 | A1 | 5/2007 | Heitzmann et al. |
| 2008/0306466 | A1 | 12/2008 | Shelton et al. |
| 2009/0227862 | A1 | 9/2009 | Smith et al. |
| 2009/0275815 | A1 | 11/2009 | Bickoff et al. |
| 2010/0262206 | A1 | 10/2010 | Zdeblick et al. |
| 2011/0190681 | A1 | 8/2011 | Cazzini |
| 2012/0059236 | A1 | 3/2012 | Pinezi |
| 2014/0088442 | A1 * | 3/2014 | Soykan ................. A61B 5/6866 600/483 |
| 2014/0200481 | A1 * | 7/2014 | Johnson ............ A61M 5/14236 600/561 |
| 2014/0243681 | A1 * | 8/2014 | Hielscher ............. A61B 5/0075 600/476 |
| 2015/0057518 | A1 | 2/2015 | Lebel et al. |
| 2015/0099979 | A1 | 4/2015 | Caves |
| 2015/0185207 | A1 | 7/2015 | Black et al. |
| 2016/0061732 | A1 | 3/2016 | Yamada et al. |
| 2016/0278678 | A1 | 9/2016 | Valdes |
| 2017/0124276 | A1 | 5/2017 | Tee |
| 2017/0202494 | A1 * | 7/2017 | Tangrea ............. A61B 5/14546 |
| 2017/0281025 | A9 | 10/2017 | Glover et al. |
| 2018/0177486 | A1 | 6/2018 | Gifford, III et al. |
| 2018/0263515 | A1 | 9/2018 | Raval |
| 2019/0022428 | A1 | 1/2019 | Maharbiz et al. |
| 2019/0358387 | A1 | 11/2019 | Elbadry |
| 2020/0155003 | A1 | 5/2020 | Mitchell |
| 2020/0179669 | A1 | 6/2020 | Mitchell |
| 2020/0291463 | A1 | 9/2020 | Vo-Dinh |

FOREIGN PATENT DOCUMENTS

| | | | |
|---|---|---|---|
| EP | 2554213 | A1 | 8/2011 |
| EP | 2425770 | A1 | 3/2012 |
| EP | 2859911 | A1 | 10/2013 |
| EP | 2859911 | A1 | 4/2015 |
| WO | 2009046439 | A2 | 4/2009 |
| WO | 2017024051 | A1 | 2/2017 |
| WO | 2018217633 | A1 | 11/2018 |
| WO | 2020106804 | A1 | 5/2020 |
| WO | 2020106842 | A1 | 5/2020 |

OTHER PUBLICATIONS

"Extended European Search Report", Appln. No. 20840471.5, European Patent Office, dated Jul. 28, 2022, pp. 1-10.

J. Hassan et al., "A microfluidic biochip for complete blood cell counts at the point-of-care", Technology (Singap World Sci). Author manuscript; available in PMC, Feb. 21, 2016, pp. 1-25.

D. Satake et al., "A sensor for blood cell counter using MEMS technology", Sensors and Actuators B: Chemical, vol. 83, Issue 1-3, Mar. 15, 2020, pp. 1-1.

K. Murakawa et al., "A Wireless Near-Infrared Energy System for Medical Implants", IEEE Xplore, pp. 70-72.

P.F. Castro et al., "A Wireless Pressure Sensor for Monitoring Pulmonary Artery Pressure in Advanced Heart Failure: Initial Experience", the Journal of Heart and Lung Transplantation, Jan. 2007, pp. 85-88.

L. Yu et al., "Chronically Implanted Pressure Sensors: Challenges and State of the Field", Sensors www.mdpi.com/journal/sensors, Oct. 31, 2014, pp. 20620-20644.

G. Stoya et al., "Determination of autofluorescence of red blood cells (RbCs) in uremic patients as a marker of oxidative damage", Clinical nephrology 58(3):198-204—Oct. 2002, pp. 1-2.

D.S. Echt et al., "Feasibility and safety of a novel technology for pacing without leads", Heart Rhythm Society vol. 3, No. 10, Oct. 2006, pp. 1202-1206.

S. Sacchi et al., "Hemodynamic Sensor in Cardiac Implantable Electric Devices: the Endocardial Accelaration Technology", Journal of Healthcare Engineering • vol. 4 • No. 4 • 2013 p. 453-464, Jul. 2013.

B.P. Yakimov et al., "Label-free characterization of white blood cells using fluorescence lifetime imaging and flow-cytometry: molecular heterogeneity and erythrophagocytosis [Invited]", Biomedical Optics Express, vol. 10, No. 8, Aug. 1, 2019, pp. 4220-4235.

M. Monici et al., "Natural fluorescence of white blood cells: spectroscopic and imaging study", Journal of Photochemistry and Photobiology B: Biology 30, Mar. 20, 1995, pp. 29-37.

Bioiptics World Editors, "Optical sensor-driven device can count white blood cells through the skin", BioOptics World, Oct. 1, 2015, pp. 1-4.

A.B. Amar et al., "Power Approaches for Implantable Medical Devices", Sensors www.mdpi.com/journal/sensors, Nov. 13, 2015, pp. 28889-28914.

R. Han et al., "Recent Advances in Super-Resolution Fluorescence Imaging and Its Applications in Biology", Journal of Genetics and Genomics 40 (2013) pp. 583-595, Nov. 23, 2013.

(56) References Cited

OTHER PUBLICATIONS

B. Dong et al., "Stochastic fluorescence switching of nucleic acids under visible light illumination", Optics Express, vol. 25, No. 7, Apr. 7, 2017, pp. 7929-7944.

M.L. Cohen et al., "Superior vena caval blood flow velocities in adults: a Doppler echocardiographic study", J Appl Physiol (1985). Jul. 1986;61(1), pp. 215-219.

B.Dong et al., "Superresolution intrinsic fluorescence imaging of chromatin utilizing native, unmodified nucleic acids for contrast", PNAS | Aug. 30, 2016 | vol. 113 | No. 35, pp. 9716-9721.

J.E. Ferguson et al., "Wireless communication with implanted medical devices using the conductive properties of the body", Expert Rev Med Devices Author manuscript; available in PMC Sep. 5, 2014, pp. 1-14.

PCT/US 20/42626, "Notification of Transmittal of the International Search Report and the Written Opinion of the International Searching Authority, or the Declaration", ISA, dated Oct. 16, 2020, pp. 1-17.

* cited by examiner

IMPLANTABLE VENOUS ACCESS PORT WITH REMOTE PHYSIOLOGICAL MONITORING CAPABILITIES

CROSS-REFERENCES TO RELATED APPLICATIONS

This application claims the benefit of U.S. Provisional Patent Application No. 62/875,182 entitled "IMPLANTABLE VENOUS ACCESS PORT WITH REMOTE PHYSIOLOGICAL MONITORING CAPABILITIES" and filed on Jul. 17, 2019, for Cathy Skinner, which is incorporated herein by reference to the extent legally permitted.

FIELD

This invention relates to medical devices and more particularly relates to a system, apparatus, and method for an implantable venous access port with remote physiological monitoring capabilities.

BACKGROUND

Implantable venous access ports ("IVAPs"), also known as subcutaneous ports, are surgically placed into a blood vessel, and frequently used in chronically ill patients who require long term access to the central venous system. IVAPs are commonly used for the following purposes: administration of drugs such as antibiotics, chemotherapy agents, or other IV drugs; administration of fluids, nutrients, or blood products; and/or blood collection for diagnostic purposes. Using IVAPs for recurrent access to the central venous system minimizes repeated needle insertion into the small veins of a patient's arms or hands leading to reduced vein scarring, narrowing, and collapse, as well as minimizing overall discomfort to the patient.

SUMMARY

An apparatus for an implantable venous access port with remote physiological monitoring capabilities is disclosed. A system and method also perform the functions of the apparatus. In one embodiment the apparatus includes a chemotherapy access port, a plurality of sensors integrated with the chemotherapy access port, where the plurality of sensors are configured to determine one or more chemotherapy-related physiological indicators and the one or more physiological indicators include at least parameters selected from red blood cell count, white blood cell count, platelets, and/or ejection fraction. The apparatus further includes a communications module integrated with the chemotherapy access port, where the communications module is configured to communicate the one or more chemotherapy-related physiological indicators to a computing device.

A method is disclosed that includes determining, based on input from a plurality of sensors integrated with a chemotherapy access port, one or more chemotherapy-related physiological indicators, the one or more physiological indicators including at least parameters selected from red blood cell count, white blood cell count, platelets, and/or ejection fraction; and communicating, using a communications module integrated with the chemotherapy access port, the one or more chemotherapy-related physiological indicators to a computing device.

A system is disclosed that includes a chemotherapy access port; and a hardware device integrated with the chemotherapy access port, the hardware device including: a processor; a memory; a power source; an autofluorescence sensor including a source configured to generate and emit excitation light within a predefined light wavelength and two or more photosensors configured to detect, record, and quantify autofluorescence emitted by the red blood cells, the white blood cells, and/or the platelets in response to the excitation light to get a red blood cell count, a white blood cell count, a platelet count, and/or ejection fraction information; and a communications module integrated with the chemotherapy access port and operably coupled to the processor, where the communications module is configured to communicate the red blood cell count, the white blood cell count, the platelet count, and/or the ejection fraction information to a computing device.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not, therefore, to be considered to be limiting of its scope, the invention will be described and explained with additional specificity and detail through the use of the accompanying drawings, in which.

DETAILED DESCRIPTION

Figure 1A:
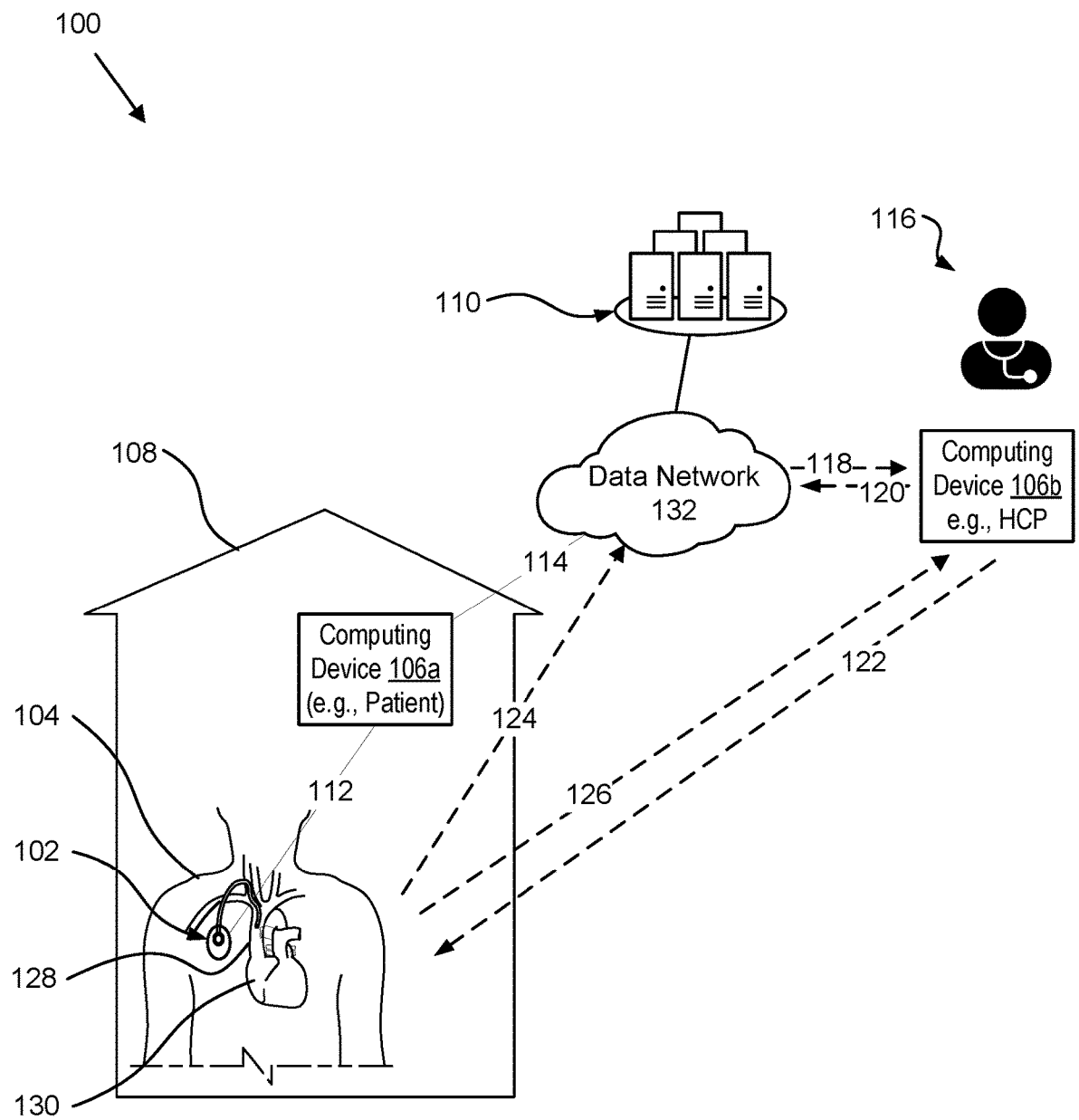
FIG. 1A depicts an embodiment of a system for an implantable venous access port with remote physiological monitoring capabilities.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to emphasize their implementation independence more particularly. For example, a module may be implemented as a hardware circuit comprising custom VLSI circuits or gate arrays, off-the-shelf semiconductors such as logic chips, transistors, or other discrete components. A module may also be implemented in programmable hardware devices such as field-programmable gate arrays, programmable array logic, programmable logic devices, or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture ("ISA") instructions, machine instructions, machine-dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, through the Internet using an Internet Service Provider). In some embodiments, electronic circuitry including, for example, programmable logic circuitry, field-programmable gate arrays ("FPGA"), or programmable logic arrays ("PLA") may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or another device to cause a series of operational steps to be performed on the computer, other programmable apparatus or another device to produce a computer implemented process, such that the instructions which execute on the computer, other programmable apparatus, or other device implement the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods, and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C." As used herein, "a member selected from the group consisting of A, B, and C and combinations thereof" includes only A, only B, only C, a combination of A and B, a combination of B and C, a combination of A and C or a combination of A, B, and C.

The present invention relates to implantable venous access ports, typically intended for chest ports comprising a catheter that is inserted into a vein. Vascular access ports (also sometimes referred to as IVAPs), are considered to be a broader genus of access ports capable of being surgically placed into a blood vessel including arterial vessels. IVAPs generally include a small reservoir (also called a portal) made of plastic or metal that contains a septum for needle insertion.

The portal is an implant typically intended for use greater than 30 days, which is placed under the skin of the chest or arm during surgery with the septum positioned in the body such that access to it is easily attained. The reservoir is connected to a thin tube (also called a catheter) that is surgically inserted into a large vein (usually the jugular or subclavian vein) which extends to the superior vena cava or the right atrium. Special needles are inserted through the skin into the septum to access the IVAP. Typically, the septum is made of rubber, metal, polyurethane, or a silicone bubble.

IVAPs vary in shape and size, however, they are often generally about the size of a US quarter dollar coin. They may be circular, oval, rectangular, or triangular shaped and often contain either one or two portals. A single lumen IVAP contains only one access point and is the most commonly used IVAP because it can be punctured roughly 1,000-2,000 times. Double lumen IVAPs contain two access points and are less commonly used, however, they are used for patients that need to receive frequent simultaneous administration of different drugs or fluids, or in scenarios where patients may need more than 2,000 port accesses over the treatment period.

Regular monitoring of physiological parameters is important in chronically ill patients, particularly cancer patients who are receiving cytotoxic or immunomodulating therapies and who are potentially immunosuppressed. Additionally, monitoring a patient's physiological responses (e.g. body temperature, heart rate and variability, infection, sleep, oxygen levels, glucose, and cortisol, etc.) before and after therapy infusion would be a desirable method to determine if the patient is benefiting from the current treatment strategy. Current methods for monitoring a patient's physiological parameters primarily focus on the use of external measurement devices such as thermometers (oral, rectal, axillary, ear, or temporal), electrocardiograms (ECG), blood pressure cuffs, and laboratory-based blood analysis.

While these methods are usually effective in hospital settings due to continuous professional healthcare compliance, it may be critical that these parameters are accurately monitored in both inpatient and outpatient settings. Furthermore, surveys from oncologists have suggested that more frequent monitoring of a patient's physiological parameters in both inpatient and outpatient settings may allow healthcare providers to detect adverse effects sooner and potentially avoid further complications from treatment in their cancer patients.

To address this need, the invention herein provides an implantable venous access port (IVAP) device which contains a plurality of sensors for continuous physiological parameter monitoring and an optionally embedded microprocessor which may be configurable to collect, analyze, store, and transmit the physiological data over standard computer networks. Optionally, in any embodiment, the processor may be configured either onboard or separately from the IVAP device. The microprocessor contains a wireless transmitter that may also be capable of transmitting the stored physiological data via encrypted wireless communication links to a secure local computing device. The local computing device will transmit the physiological data to a central server via encrypted wireless communication links. Healthcare providers and patients may securely access patient data from the server using a designated platform upon subject authentication.

In certain embodiments, the remote monitoring system may be configured to send patient health alerts to the healthcare provider. Physiological parameter thresholds are configurable to be set by the healthcare provider using the designated platform. It may be noted by one of skill in the art that research and other disease interventions show that remote patient monitoring be beneficial to patients. Thus, the apparatus, system, and methods described herein provide opportunities not found in existing systems to monitor physiological parameters of a patient. When these parameters deviate from the set thresholds for a designated period of time, alert messages are generated by the platform and sent to the healthcare providers via wireless communication links (e.g. email or text message). In various embodiments, the physiological parameters to be monitored may be selected by the healthcare provider and the thresholds of what constitutes a threshold sufficient to trigger an alert may be based on research norms in the relevant field. In some embodiments, data from the apparatus, system, and methods disclosed herein may provide data that upon proper authorization may be entered into a patient's electronic medical records ("EMR").

Provided herein is an implantable venous access port system comprising: a portal unit comprising a self-sealing septum, a power source, a plurality of physiological sensing devices or sensors, a micro-processing unit and a catheter; wherein the septum provides access to the catheter, wherein said catheter attaches proximally to the portal unit and extends distally into a venous blood pool, and wherein the distal end of the catheter contains at least one physiological sensing device, wherein the sensing device(s) provide data to the micro-processing unit and the telemetry unit transmits said data to a remote monitoring unit.

Among the benefits may be provided by this apparatus, system and methods of the present disclosure are the following:

In a first aspect, remote monitoring of physiological parameters associated with a implantable venous access port may improve patient self-efficacy. Self-efficacy refers to an individual's belief in his or her capacity to execute behaviors necessary to produce specific performance attainments. For example, by providing a readily accessible and ongoing monitoring of physiological conditions that may affect chemotherapy treatment protocols, the system communicates messages that enable a person to communicate with their healthcare provider and or to take other actions based on outputs provided by the system for example, by providing quantitative data on a regular basis that may be compared with recently established baseline levels, a patient has information in confidence necessary to contact their healthcare provider in response to one or more outputs of the implantable venous access port device Cancer patients who go through chemotherapy feel anxiety, fear, confusion, powerlessness, pain, and fatigue. The use of apparatus, system is disclosed herein empowers them to know what is "normal" and "not normal" during their treatment. They become responsive and responsible partners in their care and they monitor their progress relative to demographic-based norms for treatment. The hypothesis is that there will be a positive association between self-efficacy and understanding the cancer treatment, the impact of treatment on the body, and the enhanced relationship with the medical team and the patient.

In a second aspect, the apparatus, system, and methods disclosed herein may improve health literacy, access and support to decrease costs. Certain important goals for patients with chronic diseases include to avoid complication, prevent deterioration and maintain function. Several factors such as attitude, knowledge and skills, and support and beliefs can influence one's health behaviors. Many factors such as personal, psychological and treatment regimens can be facilitators and barriers to ongoing self-management. Furthermore, self-efficacy enhances engagement in health-promoting activities and adherence to treatment regimens and that finding ways to boost self-efficacy should be a priority.

In a third aspect, the apparatus, system and methods disclosed herein may improve health literacy. Although passive educational support, such as providing literature, can improve self-efficacy and outcomes, it is not appropriate when health literacy is a factor. Often patients are overwhelmed with a new diagnosis and new information and not understanding this information can compound the patient's stress. This reinforces that it is pertinent for providers to understand the needs of the patient individually and providers should probe patients thoroughly to determine the appropriate interventions and improve self-efficacy.

In a fourth aspect, the apparatus, system and methods disclosed herein may help address the issue of lack of access. Lack of access and geographical isolation restricts timely care of patients, and furthermore, rural residents have lower rates of treatment adherence and higher rates of mortality than their urban counterparts. Rural patients who have implantable venous access port with remote physiological monitoring capabilities, In a fifth aspect, the apparatus, system, and methods disclosed herein may beneficially provide a degree of remote support: it has been said that a person's self-efficacy can directly influence behavior change and encouragement or discouragement received from one's social support system has an impact on this. Insight into a patient's perceived difficulties can be valuable for a clinician to enhance their interaction with patients and improve efficacy.

Patient-centered care cannot be a one-size-fits-all approach and organizations need to actively promote self-management through strategies that improve and sustain self-efficacy. In the past what was considered new technology has been proven to enhance traditional patient education and reach more patients than ever before. Boosting self-efficacy could potentially be a way to increase treatment adherence and outcomes and decrease cost. By improving the timeliness of patient awareness of physiological conditions associated with chemotherapy, In a sixth aspect, the apparatus, system and methods described herein may provide beneficial cost reduction. By enabling self-efficacy in chemotherapy treatment through in vivo monitoring of physiological conditions, unnecessary laboratory visits scheduling of further treatments may be optimized so forth. The apparatus, system, and methods disclosed herein provides the necessary data using in vivo sensing to support a predictive analytics framework and passive data collection on patient numbers based on biology, not merely self-reported patient symptoms.

Figure 1B:
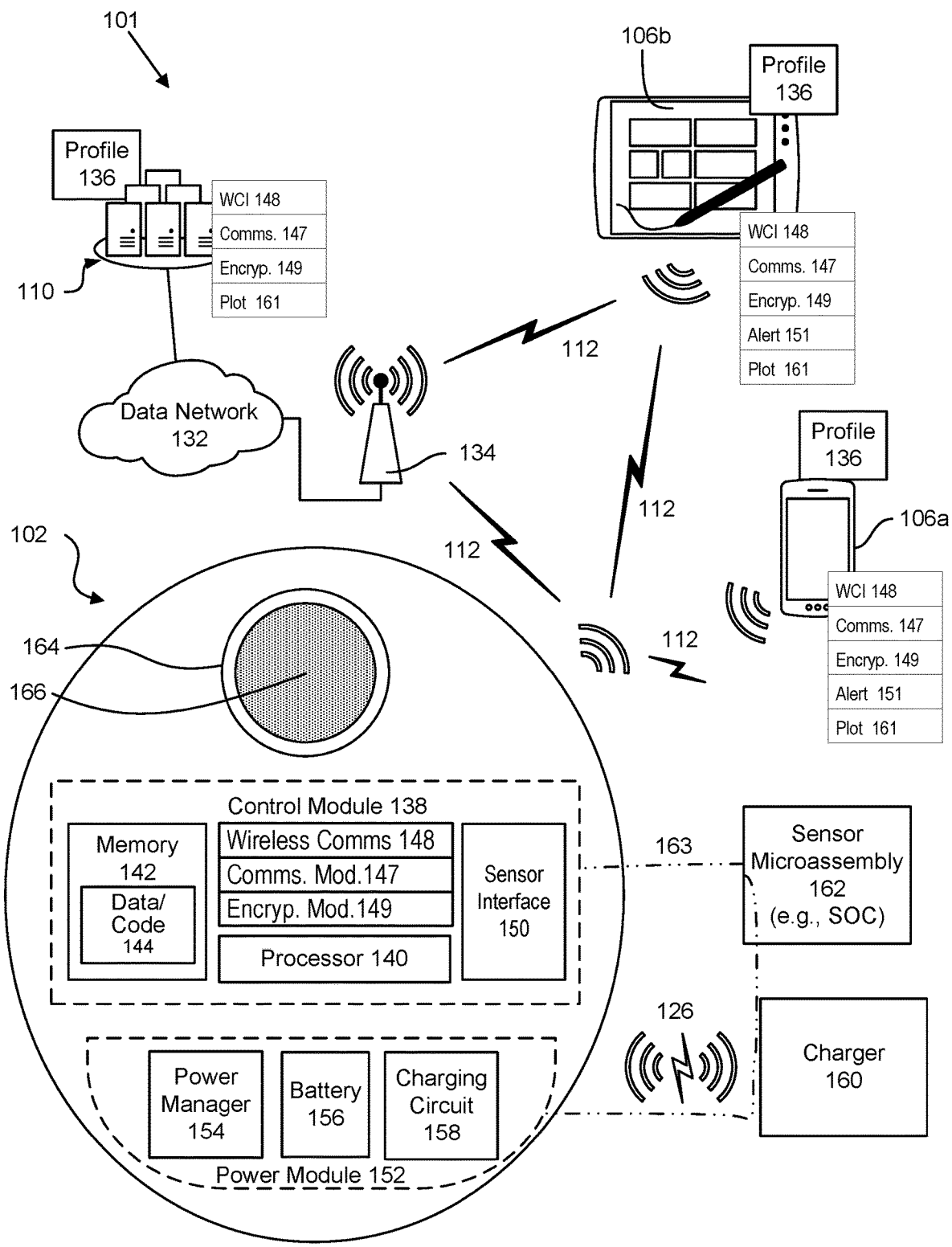
FIG. 1B depicts another embodiment of a system for an implantable venous access port with remote physiological monitoring capabilities.

FIG. 1A is a schematic representation of the remote monitoring system 100 that is an exemplary embodiment of the subject matter disclosed herein. FIG. 1B is a schematic block diagram illustrating one embodiment of a system 101 for an IVAP device 102 with various integrated physiological sensors for monitoring a patient's physiological state. The remote monitoring system includes an IVAP device 102 implanted in the patient 104 as well as the local computing device 106a inside of the patient's home 108 and the central server 110 located outside of the patient's home. It may be noted by one of ordinary skill in the art that the central server 110 may be implemented as a virtual machining server, physical server, cloud-based services, or distributed online server type services.

In some cases, the local computing device 106a may also be carried on the patient directly to facilitate portability, as opposed to being stationed within the home. The IVAP device 102 transmits the recorded physiological data to the local computing device via a wireless communication link 112 using the data network 132 which in some embodiments may be accessed via one or more access points as described below with respect to FIG. 1B.

The local computing device 106a may include various types of devices such as, but not limited to, one or more of a desktop computer, a laptop computer, a tablet computer, a smart phone, a smart speaker (e.g., Amazon Echo®, Google Home®, Apple HomePod®), an Internet of Things device, a security system, a set-top box, a gaming console, a smart TV, a smart watch, a fitness band or other wearable activity tracking device, an optical head-mounted display (e.g., a virtual reality headset, smart glasses, or the like), a High-Definition Multimedia Interface ("HDMI") or other electronic display dongle, a personal digital assistant, a digital camera, a video camera, or another computing device comprising a processor (e.g., a central processing unit ("CPU"), a processor core, a field programmable gate array ("FPGA") or other programmable logic, an application specific integrated circuit ("ASIC"), a controller, a microcontroller, and/or another semiconductor integrated circuit device), a volatile memory, and/or a non-volatile storage medium, a display, a connection to a display, and/or the like.

In one embodiment, the local computing device 106a transmits the data to the central server 110, e.g., a data center, a cloud storage system, or another remote device, via an encrypted communication network connection 114 to a data network 132 for long-term storage. The data network 132, in one embodiment, includes a digital communication network that transmits digital communications. The data network 132 may include a wireless network, such as a wireless cellular network, a local wireless network, such as a Wi-Fi network, a Bluetooth® network, a near-field communication ("NFC") network, an ad hoc network, and/or the like. The data network 132 may include a wide area network ("WAN"), a storage area network ("SAN"), a local area network ("LAN") (e.g., a home network), an optical fiber network, the internet, or another digital communication network. The data network 132 may include two or more networks. The data network 132 may include one or more servers, routers, switches, and/or other networking equipment. The data network 132 may also include one or more computer readable storage media, such as a hard disk drive, an optical drive, non-volatile memory, RAM, or the like.

The wireless connection may be a mobile telephone network. The wireless connection may also employ a Wi-Fi network based on any one of the Institute of Electrical and Electronics Engineers ("IEEE") 802.11 standards. Alternatively, the wireless connection may be a Bluetooth® connection. In addition, the wireless connection may employ a Radio Frequency Identification ("RFID") communication including RFID standards established by the International Organization for Standardization ("ISO"), the International Electrotechnical Commission ("IEC"), the American Society for Testing and Materials® (ASTM®), the DASH7™ Alliance, and EPCGlobal™.

Alternatively, the wireless connection may employ a ZigBee® connection based on the IEEE-802 standard. In one embodiment, the wireless connection employs a Z-Wave® connection as designed by Sigma Designs®. Alternatively, the wireless connection may employ an ANT® and/or ANT+® connection as defined by Dynastream® Innovations Inc. of Cochrane, Canada.

The wireless connection may be an infrared connection including connections conforming at least to the Infrared Physical Layer Specification ("IrPHY") as defined by the Infrared Data Association® ("IrDA"®). Alternatively, the wireless connection may be a cellular telephone network communication. All standards and/or connection types include the latest version and revision of the standard and/or connection type as of the filing date of this application.

The healthcare provider 116, or another authorized user, e.g., an insurance company, hospice worker, family member, doctor, nurse, or the like, may access the central server 110 at any time via an authenticated computing device 106b via the data network 132 and secure communications links 118, 120 (e.g. software subscription, license, etc.) to obtain valuable information about the patient's vitals and make therapeutic adjustments as needed.

In some instances, if the patient is experiencing an adverse reaction, the central server 110 may generate an alert message and send it to the healthcare provider 116 immediately via the secure communication link 120 (e.g., email, text message, push notification, etc.). Based on the information provided by the alert message, the healthcare provider 116 can directly contact the patient 104, e.g., via a data network 132 such as a mobile data network using a wireless communication link 122, to adjust the therapeutic regimen.

For instance, an alert module may transmit one or more patient health alerts from the IVAP device 102, from the local computing device 106a, from a central server 110, or the like, to an authorized user in response to one or more chemotherapy-related physiological indicators being outside threshold values. In such an embodiment, the threshold values are determined based on previous measurements of the one or more chemotherapy-related physiological indicators, which may be stored on a memory integrated with the IVAP device 102. Furthermore, in some embodiments, the alert module 151 depicted in FIG. 1B is configured to transmit the one or more patient health alerts in response to the one or more chemotherapy-related physiological indicators being outside threshold values for a predefined period of time, e.g., ten minutes, an hour, a day, a week, or the like.

In some cases, the patient 104 may obtain access to their personal data on the central server 110 using an authenticated platform 124 (e.g., a web site, a mobile application, etc.). Based on the knowledge obtained by the patient 104 from their physiological data, patients can be more involved in the treatment process and contact their healthcare provider directly e.g., via a data network 132 such as a mobile data network using a wireless communication link 112 to ask questions about their diagnosis, treatment regimen, physiological measurements, and symptoms.

The IVAP device 102 with remote physiological monitoring capabilities is surgically implanted by a physician with the catheter extending into the superior vena cava 128 or the right atrium 130. The IVAP device 102 is configured to perform various functions such as, but not limited to: administration of antibiotics, chemotherapy agents, or other IV drugs; administration of fluids, nutrients, or blood products; and/or blood collection, analysis, quantification, and/or the like.

Based on the condition of the patient 104, as measured by the IVAP device 102, the therapeutic regimen (e.g., dose, delivery rate, delivery schedule, etc.) may be altered to improve the therapeutic effect or minimize complications. For example, if the patient 104 experiences a prolonged spike in heart rate or core body temperature in response to the therapeutic regimen as measured by the IVAP device 102, the dose or delivery rate may be decreased, paused, or even terminated to reduce or eliminate the adverse effect. Additionally, if the patient 104 is not observing a therapeutic benefit from the therapeutic agent as measured by the IVAP device 102, the dose or delivery rate may be increased or decreased to establish the desired therapeutic effect. As another example, the sensing of a low ejection fraction may indicate potential damage to the heart and may indicate an altered schedule for additional chemotherapy treatment or an additional treatment to address the heart concerned may be prescribed. In another example, an absolute neutrophil count that is too low may also indicate that the chemotherapy schedule should be adjusted.

While some such measurements could be taken in a clinic, continually monitoring them using the system, apparatuses, and methods described in the present disclosure provides further advantages both to the patient and to the healthcare providers. For example, many chemotherapy patients have temporarily compromised immune systems as a result of the suppressive effects of the chemotherapy on the patient's immune system. Therefore, it is advantageous to avoid unnecessary travel and contact with potential sources of infection such as might be found in waiting rooms, or traveling to a clinic. By making the measurements in vivo with the implantable apparatus and system described herein, visits to the clinic can be scheduled only when the measured data from the system of the present disclosure indicates that the clinical visit for chemotherapy treatment should proceed at the scheduled time.

It is noted that in each of the data transmissions described above between the computing devices 106a, 106b, the central server 110, users such as the patient 104 and/or the healthcare provider 116, and the IVAP device 102, an encryption module 149 as depicted in FIG. 1B may be used to encrypt the one or more chemotherapy-related physiological indicators, alerts, and/or any other communications prior to transmitting the data, information, or the like to ensure a secure and safe transmission of sensitive and confidential patient health data. It may be noted that the central server 110 may be implemented as a physical server, multiple physical servers, virtual machines, cloud-based services, and so forth and the central server 110 may in certain embodiments comprise services provided by various physical servers that are geographically distributed.

Referring in more detail to FIG. 1B and in particular to the system 101 for an IVAP device 102 with various integrated physiological sensors for monitoring a patient's physiological state, the system 101 includes an IVAP device 102, as described above, which includes a control module 138 and a power module 152, which are described in more detail below.

The control module 138, in one embodiment, includes a memory 142, which includes data/code 144 for performing various functions of the IVAP device 102, a processor 140, a wireless communications interface ("WCI") 148, a communication module 147, an encryption module 149, and a sensor interface 150. The memory 142 may include one or more volatile memory media, which may include but is not limited to random access memory ("RAM"), dynamic RAM ("DRAM"), cache, or the like, and/or one or more non-volatile memory media, which may include but is not limited to: NAND flash memory, NOR flash memory, nano random access memory (nano RAM or "NRAM"), nanocrystal wire-based memory, silicon-oxide based sub-10 nanometer process memory, graphene memory, Silicon-Oxide-Nitride-Oxide-Silicon ("SONOS"), resistive RAM ("RRAM"), programmable metallization cell ("PMC"), conductive-bridging RAM ("CBRAM"), magneto-resistive RAM ("MRAM"), dynamic RAM ("DRAM"), phase change RAM ("PRAM" or "PCM"), magnetic storage media (e.g., hard disk, tape), optical storage media, or the like.

The data/code 144 that is stored on the memory 142 may include program code, applications, executable code, compiled code, instructions, functions, libraries, and/or the like that are configured for performing various functions of the IVAP device 102 such as, for example, analyzing sensor data, quantifying sensor data, communicating with external computing devices (e.g., via the wireless communications interface 148), and/or the like.

The wireless communications interface 148 may communicate with external systems via radiofrequency signals in the ISM band (900 MHz to 2.4 GHz), such as wireless communications interfaces 148 configured for low-power short-range communication. For example in various embodiments, the wireless communications interfaces 148 may implement one or more of the various communication standards such as Wi-Fi, Bluetooth®, near-field communication, infrared, and/or the like, or long-range communication channels such as LoRa, medical telemetry, and/or the like. Other wireless communications interfaces 148 may include a mobile or cellular network interface, a satellite communication interface, and/or the like.

In certain embodiments, the wireless communications interface 148 may be configured to communicate with one or more computing devices 106a, 106b, servers 110, and/or the like are referred to as external computing devices or external data collection systems to indicate that these devices are external to the patient and/or in certain embodiments external to the patient's location or venue. Each of the computing devices 106a, 106b, and the servers 110 may include corresponding wireless communication interfaces 148 that are configured to communicate over a wireless connection 112 which may, in some embodiments, be accessed via one or more access points 134 to communicate sensor data captured by the physiological sensors in the patient's body. In various embodiments, the computing devices 106a, 106b, also include an encryption module 149 that is configured to encrypt or decrypt data communicated over the data network 132 or any of the wireless connections 112. In some embodiments, the encryption module implements HIPAA compliant encryption standards using data encryption APIs compatible with operating systems utilized by the computing devices 106a, 106b, and/or the servers 110.

The communication module 147 is configured to communicate data between the IVAP device 102, and corresponding communication modules 147 that may be implemented in one or more of the computing devices 106a, 106b, and/or the central server 110. In certain embodiments, the communication occurs over the data network 132. In some embodiments, some communication occurs point-to-point with the computing devices 106a, 106b via one or more wireless communications links 112. For example, when the patient 104 is at home, the communication module may control a wireless protocol pairing between the IVAP device 102 and the local computing device 106a such as, for example, using Bluetooth.

And although FIG. 1a depicts the computing device 106B as being a remote or external computing device, the communication module may be configurable to connect to the computing device 106b being used by healthcare provider via a direct local communication link 122 may be established with the computing device 106 being used by a healthcare provider. One example may include enabling the clinician to interrogate the IVAP device 102 during chemotherapy or during other clinical treatments or activities. Another example of using local communications may be enabling the clinician to perform a firmware update or install an application for the IVAP device 102.

In at least one embodiment, the control module 138 includes a sensor interface 150 that is configured to communicate with various physiological sensors that are integrated into the IVAP device 102. In such an embodiment, the sensor interface 150 is configured to communicate the one or more chemotherapy-related physiological indicators to a computing device, e.g., a central server 110 via a data network 132, a health care professional's device 106b, a local computing device 106a, and/or the like. In various embodiments, the sensor interface 150 includes a power bus that is included with the sensor connection 163 that supplies power to the sensor microassembly 162, as well as a data bus included in the sensor connection 163 for communicating data between the sensor microassembly 162 and the sensor interface 150. In some embodiments, this interface may be configured to use the inter-integrated circuit ("I2C") protocol which is a half-duplex bidirectional two-wire bus system for serial communication between different devices. In other embodiments, the data bus may be implemented using photodiodes and LEDs optically coupled to each other using fiber-optic leads.

As explained above, the IVAP device 102 may be a chemotherapy access port that includes a plurality of sensors that are integrated with, operably or communicatively coupled to, and/or otherwise connected to the chemotherapy access port. The sensors may be part of a sensor microassembly 162 (shown in FIG. 1C), which may be embodied as a system on a chip such as, for example, an FPGA, an ASIC, and/or another programmable hardware device. The sensor microassembly 162 is described in further detail below with respect to FIG. 1C The power module 152 may include a power manager 154, a battery 156, and a charging circuit 158. The power manager 154 may be configured to manage and maintain the power supply that the battery 156 supplies for the various components of the control module 138 and/or the sensor microassembly 162.

The battery 156, in certain embodiments, may include a rechargeable battery, e.g., a Lithium-ion battery, that is configured to provide power to the various components of the control module 138 and/or the sensor microassembly 162. The charging circuit 158 may be configured to (re)charge the battery 156 while the IVAP device 102 is placed within the patient 104.

The charger 160 may be connected to the control module 138 via a wireless charging connection 126, e.g., an inductive coupling connection. In such an embodiment, the charging circuit 158 may comprise an induction receiver and the charger 160 may be a device configured for wireless power transfer such as a charging station, inductive pad, or the like. For example, the charger 160 may use the Qi wireless charging standard for power transfer between the charger 160 and the charging circuit 158.

In certain embodiments, the charging circuit 158 comprises a photocell array panel that produces current to charge the battery 156 in response to being illuminated through the patient's skin by a light source. In such embodiments, the charger 160 may include a light source such as an LED or LASER diode emitting light in the spectrum from 500 nm to 1000 nm to illuminate the photocell array panel of the charging circuit 158. One advantage of the light charging technology as compared to inductive charging is that the infrared charging technology may generate less heat inside the subcutaneous pocket 214 (depicted below in FIG. 2B).

In certain embodiments, the IVAP device 102 includes a port 164 for inserting, providing, injecting, or the like medicines, drugs, chemicals, or the like into a patient 104, e.g., chemotherapy drugs. The port 164 may include a septum 166 where a needle or other injection device is inserted for administering fluids, e.g., medicines or drugs. It may be noted that the septum 166 is self-healing meaning that when an injection device is inserted and subsequently removed, upon removal, the septum seals itself such that liquid does not leak from the port 164 into the subcutaneous pocket 214.

Moreover, in some embodiments, the patient 104 may have a profile 136 that contains health information about the patient 104, including sensor parameters based on previous readings of the patient's physiological state based on the sensor input data. In some embodiments, the profile may be stored in the cloud e.g., in the central server 110. In other embodiments, the user profile may be stored on a computing device being used by a healthcare provider (such as the computing device 106*b*). In various embodiments, the profile 136 may include information entered by the patient and/or the healthcare provider.

Figure 1C:
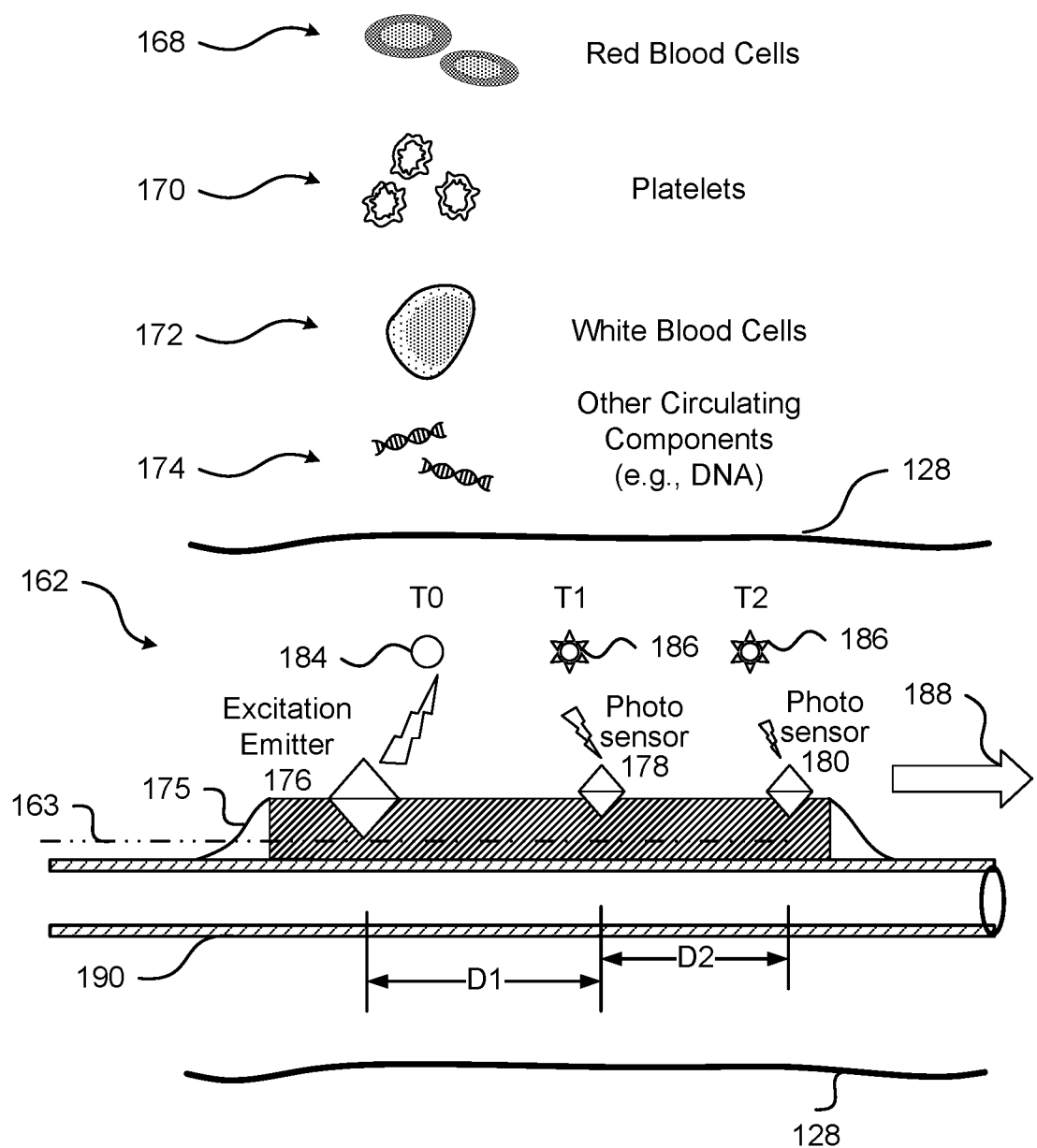
FIG. 1C depicts an embodiment of a micro-sensor assembly for an implantable venous access port with remote physiological monitoring capabilities.

For instance, information about a patient's blood cell counts or other physiological parameters that the sensors on the sensor microassembly 162 as depicted in FIG. 1C measures may be stored and accessed as part of a patient's profile 136.

FIG. 1C depicts a schematic illustration of a sensor microassembly 162, as described above with reference to FIG. 1B. In one embodiment, the sensor microassembly 162 is embodied as an electronics module, a system on a chip ("SOC"), or the like and is coupled to a catheter 190 or cannula. The sensor microassembly 162, in one embodiment, is powered via a sensor connection 163. The sensor connection 163 may be connected to both the control module 138 and the power module 152. The sensor microassembly 162, in certain embodiments, is in communication with the control module 138 via the sensor connection 163 for receiving instructions, functions, directions, program code, or the like and for transmitting sensor data, values, information, calculations, quantifications, and/or the like based on physiological data received from one or more sensors on the sensor microassembly 162.

Figure 2A:
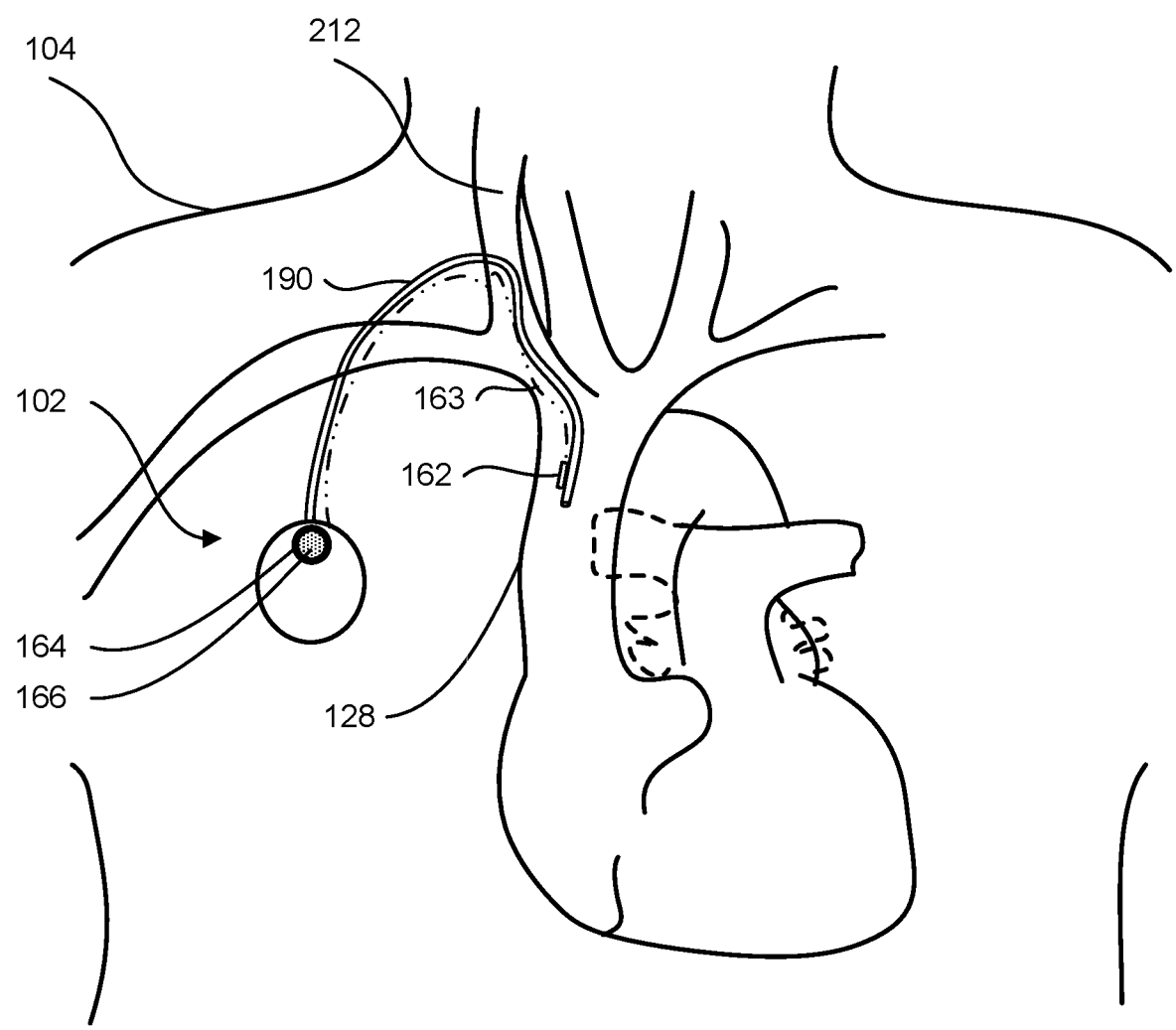
FIG. 2A depicts an embodiment of an IVAP for an implantable venous access port with remote physiological monitoring capabilities.

In one embodiment, the sensor microassembly 162 is placed within a vein of the patient 104, such as the superior vena cava 128, as shown and explained respectively with reference to FIG. 2A. In this manner, the sensor microassembly 162 depicted in FIG. 1B is placed directly in the bloodstream for measuring various elements in the blood as it flows 188 through the superior vena cava 128 and for transmitting the measured information back to the control module 138. For example, the sensors may be configured to detect and measure various circulating elements in the bloodstream such as red blood cells 168, platelets 170, white blood cells 172, and/or other circulating components 174 such as DNA, proteins, cancer cells and/or the like.

In one embodiment, the sensor microassembly 162 includes a plurality of sensors configured to determine one or more chemotherapy-related physiological indicators. The one or more physiological indicators comprising at least parameters selected from red blood cell count, white blood cell count, platelets, and/or ejection fraction. The sensor microassembly 162, however, may include different sensors for measuring various physiological conditions, parameters, elements, or the like.

In one embodiment, the plurality of sensors includes a blood cell counting sensor that is configured to determine the red blood cell count, the white blood cell count, and/or the platelet count of a patient. In certain embodiments, the blood cell counting sensor comprises an autofluorescence sensor 175 configured to perform an in-vivo count of red blood cells 168, white blood cells 172, and platelets 170.

It may be noted that certain types of cancer such as leukemia and/or lymphoma, indicative autofluorescence signatures may be detected based on degree of cell differentiation, size, morphology or other differences between cancer cells and normal cells. For example, in acute lymphoblastic leukemia, the cancer is found in the blasts which have not differentiated, and which exhibit an autofluorescence signature that is different from the differentiated white blood cells which develop from normal noncancerous blasts. Accordingly, using the apparatus, systems, and methods described herein, the autofluorescence signature of an excess of blasts may be detected as an indicator of a possible increase or relapse of the acute lymphoblastic leukemia.

Cells may exhibit autofluorescence attributed to their protein and nucleic acid content and the distribution of such composites within the cell. The subject matter herein, therefore, leverages the autofluorescence of blood cells to perform an in-vivo total and differential count of blood cells including red blood cells and white blood cells.

In various embodiments, the autofluorescence sensor 175 may be an apparatus that may include various types of components such as, for example, emitters, temperature sensors, and so forth. In other words, in some embodiments, the autofluorescence sensor 175 is capable of detecting autofluorescence and may also include other components and functions that are configured to perform various other functions besides excitation and detection of autofluorescence and certain such functions are described below with respect to detection of proteins and other non-cellular components that may be found in the blood of the patient.

In one embodiment, the autofluorescence sensor 175 includes a light source, e.g., an excitation emitter 176 (also refer to herein as a light source) that is configured to generate and emit excitation lightwithin a predefined light wavelength. In certain embodiments, the light source comprises one or more light-emitting components selected from a point source light-emitting diode ("LED"), a planar LED (such as, for example, a Chip-On-Board ("COB") component having a rectangular or another geometrically shaped perimeter, a laser diode, an optical fiber, and combinations thereof. In various embodiments, the light source is tunable to control one or more of an intensity, a frequency, a wavelength, and/or a duration. One example provider of biocompatible LEDs with broad wavelength selections that are fixed wavelength or spectrally tunable is AMS Technologies AG of Martinsried, Germany. In various embodiments, the excitation emitters 176 may be configured with planar geometries and standard components or as customized modules for inclusion in a system-on-a-chip silicon design.

The autofluorescence sensor 175 may further include a plurality of photosensors 178, 180 that are configured to detect, record, and quantify autofluorescence emitted by the red blood cells 168, the white blood cells 172, and/or the platelets 170 in response to the excitation light. As used herein, the term "photosensor" refers to an electronic component that detects the presence of visible light, infrared transmission ("IR"), and/or ultraviolet ("UV") energy.

In various embodiments, the photosensors 178, 180 are implemented as arrays. In certain embodiments, the photosensors may be silicon photodiode arrays. AMS Technologies AG is also a provider of miniaturized silicon photodiode arrays. Other similar vendors include: OSI optoelectronics of Hawthorne Calif.; Hamamatsu Photonics K.K. Hamamatsu City, Japan; and Kyoto Semiconductor of Kyoto, Japan. In certain embodiments, the photosensors 178, 180 are discrete components that are packaged into the miniature sensor microassembly 162. In some embodiments, the photosensors 178, 180 are manufactured as part of the chip fabrication process.

For example, as shown in FIG. 1C, the autofluorescence sensor 175 may trigger the excitation emitter 176 (e.g., light source) to emit light within a predefined range, e.g., within a range of about 280 nm to about 1400 nm. As used herein, the term "about" with respect to a specified range of wavelengths means the specified range extended by +/−20 nm. For instance, the excitation emitter 176 may emit ultraviolet light that has a wavelength within a range of 280 nm to 400 nm; visible light that has a wavelength within a range of 400 nm to 780 nm; and near-infrared light that has a wavelength within a range of 780 nm to 1400 nm; and/or combinations thereof.

A circulating element 184 in the blood, such as a red blood cell, may absorb, capture, or the like, the light from the excitation emitter 176 and time T0. In response, the circulating element 184 may then emit autofluorescence 186, which is detected, recorded, measured, and/or quantified at time T1 by a first photosensor 178 that is a predefined distance D1 from the excitation emitter 176 and also at time T2 by a second photosensor 180 that is a second predefined distance D2 from the first photosensor 178.

In some embodiments, the autofluorescence sensor 175 determines whether a circulating cell in the blood is a red blood cell 168, a white blood cell 172, or a platelet 170 based on one or more measurements of autofluorescence detected at the plurality of photosensors. In various embodiments, the one or more measurements may include autofluorescence magnitude, autofluorescence wavelength(s), autofluorescence decay rate, and/or combinations thereof emitted by the various cells/components in the bloodstream in response to excitation. For example, certain components in the blood such as the red blood cells 168, the white blood cells 172, and/or the platelets 170, respond to impulse of excitation energy having a predetermined shape and duration at one or more predetermined wavelengths (ultraviolet, visible, or infrared) by exhibiting autofluorescence with a particular decay rate.

As the components travel in a laminar flow with the blood past the first and second photosensors 178, 180, the velocity of travel and the decay rate can be determined. It may be noted that various types of components in the blood respond differently to different wavelengths of light thus principles of spectra photometry can also be employed together with the determination of decay rate to detect which particular types of components in the blood are present and in what concentration.

Some blood components such as proteins and other bioactive components in the blood are either too small to detect using autofluorescence or do not exhibit autofluorescence and thus other spectrophotometric methods are used to determine the presence and or concentration of such bioactive components. The absorbance and or reflectance of a particular wavelength of light emitted from the excitation emitters may be measured without needing to determine the velocity of the components in the blood flow therefore these components may be detected during the diastolic phase by measuring absorbance, reflectance, and/or optical density of blood components that are not moving at the higher flow rate associated with the systolic phase. Further details about detecting and identifying various parameters associated with the different components in blood including those that exhibit autofluorescence and those that do not exhibit autofluorescence are described in more detail below with respect to FIG. 3.

In further embodiments, as shown in FIG. 1C, the plurality of photosensors 178, 180 (e.g., at least two of the photo sensors of the plurality) are placed a predefined distance from one another, e.g., distances D1 and D2. The predefined distances and time it takes for the autofluorescence signal to be detected by the second photosensor 180 may be used to calculate various properties of the bloodstream such as a blood flow velocity, an ejection time, an ejection fraction, cardiac output, and/or combinations of the foregoing, during different phases of the cardiac cycle regardless of the intensity of such fluorescence of the pattern of change in such autofluorescence intensity. This allows for simultaneous measurement of the flow velocity of blood and counting and classifying cells as they pass tangential to the sensor microassembly 162. Additional details concerning certain example calculation of blood flow within the superior vena cava and calculation of blood flow velocity, ejection time ejection fraction, and so forth are described in more detail below with respect to FIG. 4.

FIG. 2A shows a schematic illustration of the IVAP device 102 in the chest cavity of the patient 104. In one embodiment, the IVAP device 102 includes a port 164 containing a septum 166 for needle insertion and a catheter 190. The catheter 190 begins at the port 164, is surgically inserted into a vein 212, and terminates in the superior vena cava 128. As described above, the IVAP device 102 includes a sensor microassembly 162 for measuring and monitoring physiological parameters using a plurality of sensors that are located on the outside of the catheter 190. The location of the sensor microassembly 162 allows it to obtain measurements from the mixed venous bloodstream in the lumen of the superior vena cava 128. To detect the signal from each sensor of the sensor microassembly 162, in one embodiment, each sensor is connected to a microprocessor located on the port 164 through leads which form a sensor connection 163 that runs along the catheter 190. In certain embodiments, to avoid any concerns about the sensor connection 163 interfering with the flow of fluid e.g., chemotherapy medication, in the lumen of the catheter 190, a second tube or lumen is coupled with the catheter 190 so that there are two conduits coupled together. In other words, the catheter 190 and the conduit through which the sensor connection 163 passes are coupled together.

Figure 2B:
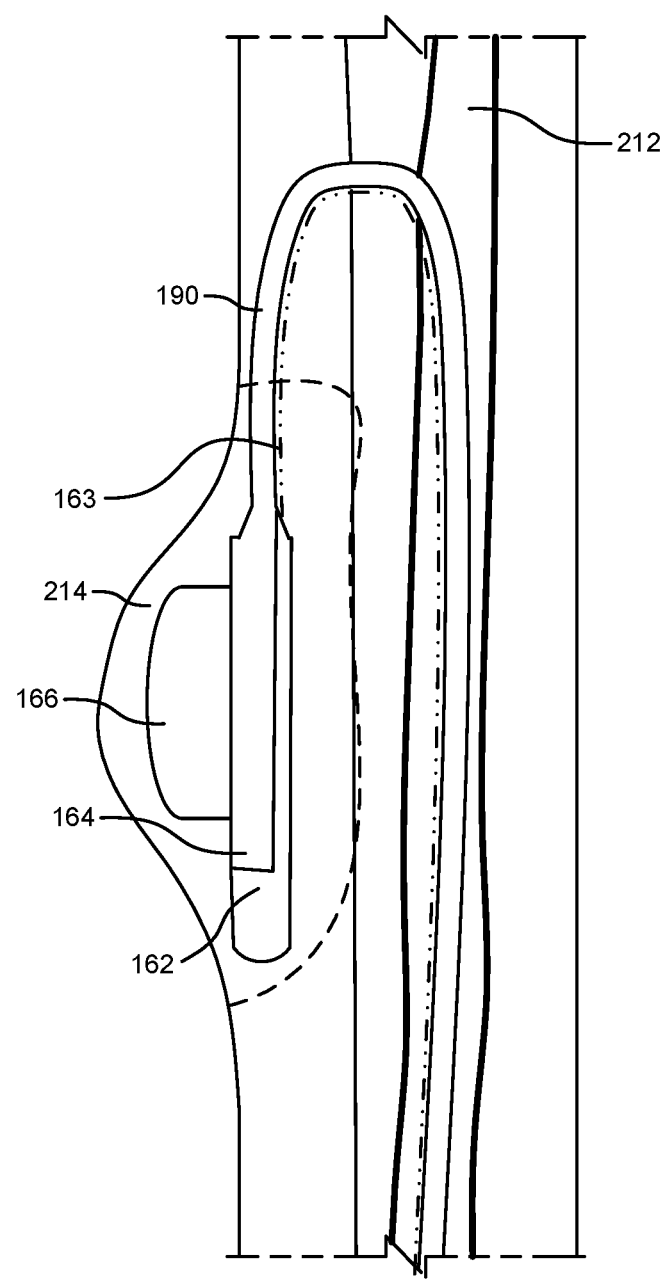
FIG. 2B depicts another embodiment of an IVAP for an implantable venous access port with remote physiological monitoring capabilities.

FIG. 2B illustrates a lateral view of the IVAP device 102 in the subcutaneous pocket 214 of the chest cavity. In this perspective, the control module 138 and the power module 152, which designates how the implantable device analyzes, stores, and transmits physiological data to an external source, as described above, are visibly located on the base of the port 164. Since these elements of the IVAP device 102 do not need access to the bloodstream, they may be located elsewhere on the IVAP device 102 and are not restricted to the base of the port 164. In various embodiments, the sensor connection 163 (depicted as a dash-dot-dot line) passes through a flexible biocompatible conduit coupled to the catheter 190.

Figure 3:
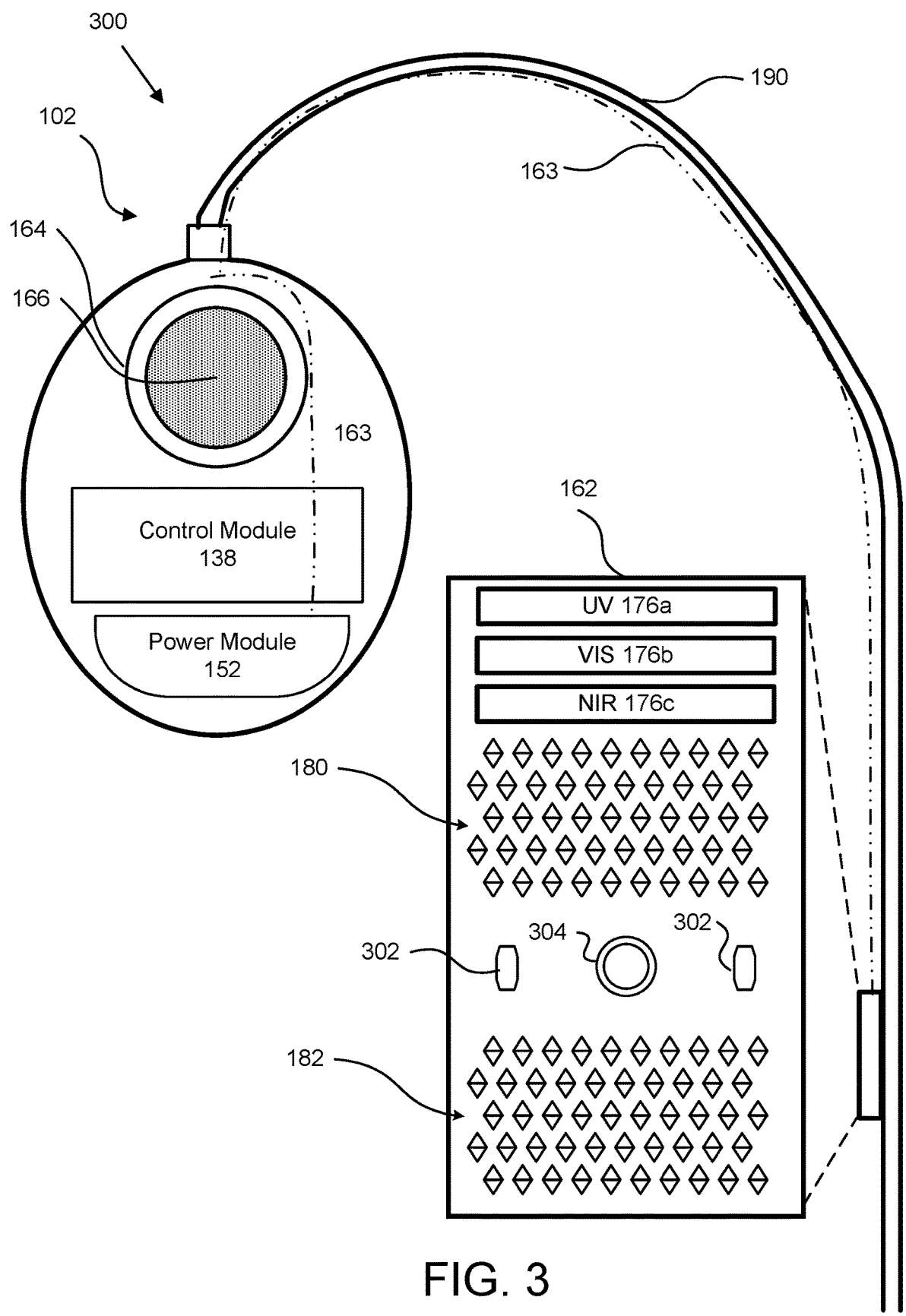
FIG. 3 depicts another embodiment of an IVAP for an implantable venous access port with remote physiological monitoring capabilities.

FIG. 3 is a schematic diagram of one embodiment of an implantable venous access port 300 in accordance with the subject matter described herein. In one embodiment, the implantable venous access port 300 includes an embodiment of an IVAP device 102, as described above, that includes a port 164 and a septum 166 for injecting fluids, e.g., chemotherapy drugs, directly into the patient 104. The IVAP device 102 includes a control module 138 and a power module 152, as described above with reference to FIG. 1B.

The control module 138 and the power module 152 are coupled to a sensor microassembly 162 via a catheter 190 and a sensor connection 163. The sensor microassembly 162 is placed, via the catheter 190, into a bloodstream of a vein of a patient 104. In one embodiment, the sensor microassembly 162 includes a plurality of sensors that are configured to detect, monitor, and measure circulating elements in the bloodstream and other physiological indicators and report the sensed data to the control module 138. The sensors may include blood sensors, as described above, one or more temperature sensors 302, pressure sensors 304, and/or the like.

For example, the one or more temperature sensors 302 may be made of a sensitive temperature sensing element which is at least one of the silicon-based temperature sensors, or thermistor, or radiometric temperature measurement device with the proper signal conditioning circuit to convert temperature into an analog electrical signal that is digitized inside the sensor microassembly 162 and sent to the control module 138 over the sensor connection 163. One example of a discrete miniaturized precision temperature sensor with a footprint of less than 1 mm$^2$ is the LMT70 ultrasmall high precision low-power CMOS analog temperature sensor manufactured by Texas Instruments of Dallas, Tex., USA.

One type of pressure sensor 304 suitable for medical applications is a micro-electromechanical system (MEMS) type sensor that performs electrical sensing using capacitive, piezoelectric, or piezoresistive pressure sensing elements. Various manufacturers of mems type pressure sensors for invasive uses such as catheter tip sensors provide suitable sensors for the sensor microassembly 162. Examples of MEMS pressure sensors for medical implantation include Millar, Inc. of Houston, Tex., USA. Other vendors include Silicon Microstructures, Inc., of Milpitas, Calif. USA.

As shown in FIG. 3, the sensor microassembly 162 includes multiple different excitation emitters 176 (e.g., light sources) that each generates light of different wavelengths. For example, the light sources 176 may include a UV light source 176a, a visible light source 176b, and a near-infrared light source 176c. As depicted in FIG. 3, in certain embodiments, the individual light sources 176a, 176b, 176c, are manufactured as planar light-emitting strips similar to those found in certain chip onboard LED components. In various embodiments, the individual light sources 176a, 176b, 176c, may be configured, fitted, or coupled, with one or more optical devices such as lenses, prisms, filters, to focus, direct, limit, or otherwise perform optical transformations on the light emitted from the light sources 176.

In further embodiments, the sensor microassembly 162 includes a plurality of photosensors 180, 182 that may be arranged respectively in in one or more arrays to yield spatially registered optical measurements and are configured to measure autofluorescence emitted by circulating elements in the bloodstream that have absorbed the light that is emitted from the light sources. As used herein, the term "spatially-registered" means that each measurement made by a detection element (e.g., a photosensor element) of a given array has approximately the same physical location in another array. Using "spatially-registered" measurement enables deviations from perfect detection registration to be corrected using digital image processing algorithms familiar to those of ordinary skill in the art. For example, if more than one array is emitting light, the distance between emitting elements can be determined as can the distances between sensor element and can be taken into account when determining values of a response.

In one embodiment, in addition to detecting cellular components of the blood, e.g., red blood cells, white blood cells, platelets, and/or the like, the one or more photosensors 180, 182 (which may in certain embodiments individually comprise respective arrays of photosensor elements) of the plurality of photosensors are configured to perform light-scattering measurements for quantifying non-cellular components of blood during the diastolic phase. In such an embodiment, the non-cellular components of the blood are identified based on spectral dependent optical density measurements, spectral dependent light scattering measurements, and/or spectral dependent autofluorescence intensity and lifetime measurements, and combinations thereof, as registered by at least two arrays of photosensors 180, 182 of the plurality of fluorescence sensors. In certain embodiments, the non-cellular components that are quantified comprise protein content including albumin, bilirubin, hemoglobin, myoglobin, creatinine, and/or free nucleic acids.

Other measurements may be determined based on the information from the plurality of sensors. For instance, systolic phase measurements may be derived including blood pressure, flow velocity as indicated by cellular velocity during the laminar flow, temperature, cellular morphology, classification, and count (white blood cells, red blood cells, platelets), oxygen saturation, and/or the like. Measurements on the diastolic phase may include protein measurements, nucleic acid measurements (e.g., cell-free DNA and RNA), hemodynamics of superior vena cava and major veins, Sp02 measurements (also referred to as oxygen saturation level), heart rate measurements, electrocardiography to record cardiac cycle, and detection and quantification of cell-free nucleic acids (DNA/RNA).

As it pertains to Sp02 measurements, the ratio of absorbance of red and infrared by oxygenated and deoxygenated hemoglobin is used to calculate peripheral oxygen saturation by pulse oximetry. Because the measurements are performed in the Superior Vena Cava, a transfer function is used to transform the measurements to represent oxygen saturation in the arterial system. The general form of the transfer function may be mathematically represented as $Ao(t)=f(SVC(t))$, which may be used to calculate the instantaneous flow velocity and systemic blood pressure in the aorta, respectively, based on the instantaneous flow velocity and pressure in the superior vena cava 128, as shown in FIG. 4.

Additionally, identification and qualitative/quantitative assessment of free circulating nucleic acids DNA and RNA can be performed during diastolic phase measurements to detect tissue damage. Furthermore, measuring using optical density and other photometric parameters that do not depend on autofluorescence of the circulating components such as circulating proteins including hemoglobin, bilirubin, creatinine, albumin, etc. can be performed during diastolic phase measurements because such measurements may not require a calculation of autofluorescence decay rate or other motion dependent measurement methodologies.

Figure 4:
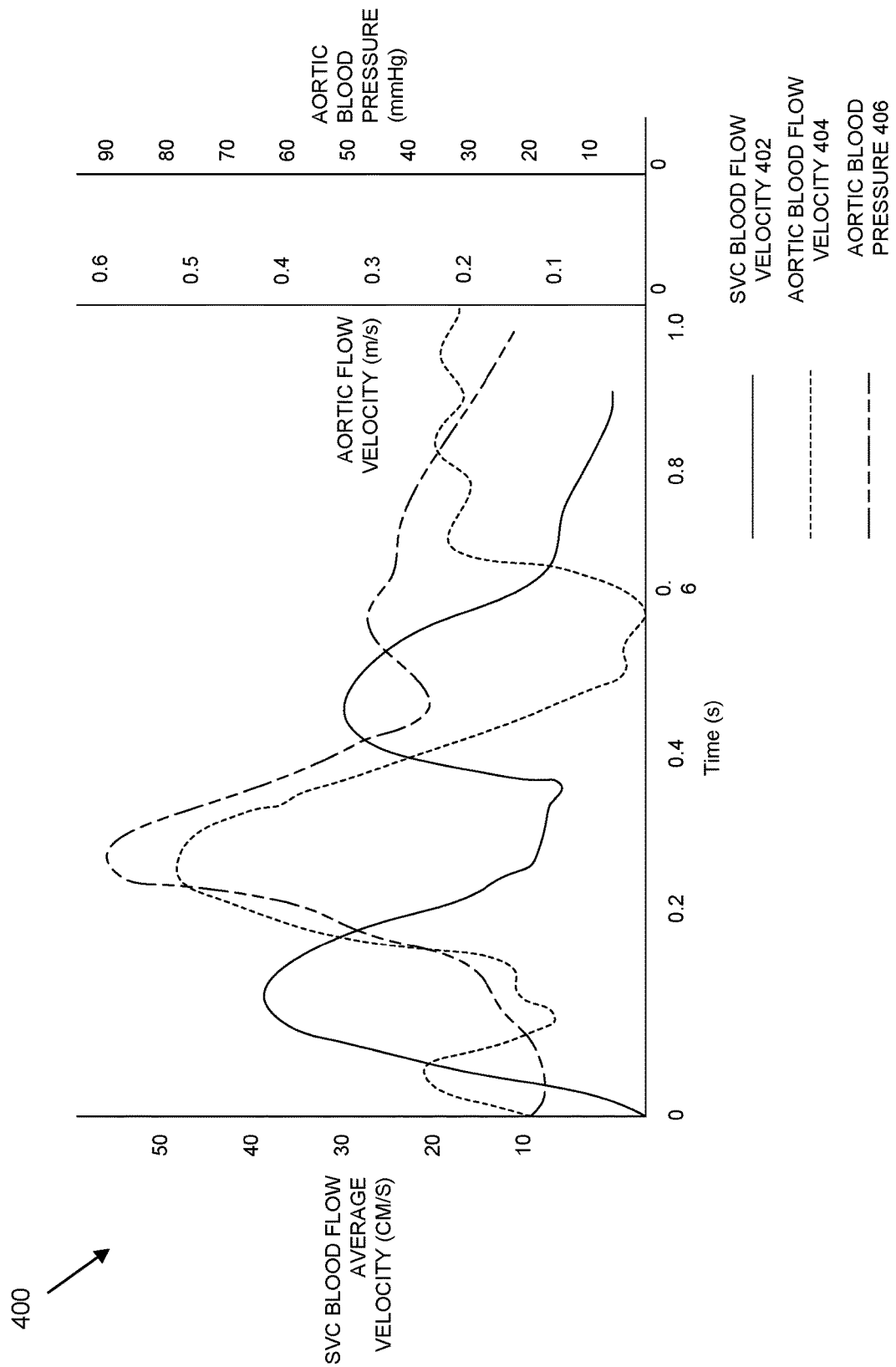
FIG. 4 depicts an example plot of results captured using an implantable venous access port with remote physiological monitoring capabilities.

FIG. 4 depicts one example output graph 400 of the various measurements taken, derived, calculated, or the like based on the data sensed by the sensors of the sensor microassembly 162. For instance, in one embodiment, a plot module 161 may generate a plot that includes a graph, over time, of the superior vena cava blood flow velocity 402, the aortic blood flow velocity 404, and the aortic blood pressure 406. Tracking these measurements can help direct the treatment plan of a cancer patient, for example, in regard to the amount, type, strength, and/or the like of the chemotherapy treatment. Other measurements may be plotted over time including the red blood cell count, the white blood cell count, the platelet count, and/or the like. In various embodiments, the plot module 161 depicted in FIG. 1B may be implemented using functions within the computing devices 106a, 106b. In other embodiments, certain portions of the plot module may be implemented in the central server 110 taken advantage of the higher computing power of cloud-based services or virtual machines.

Figure 5A:
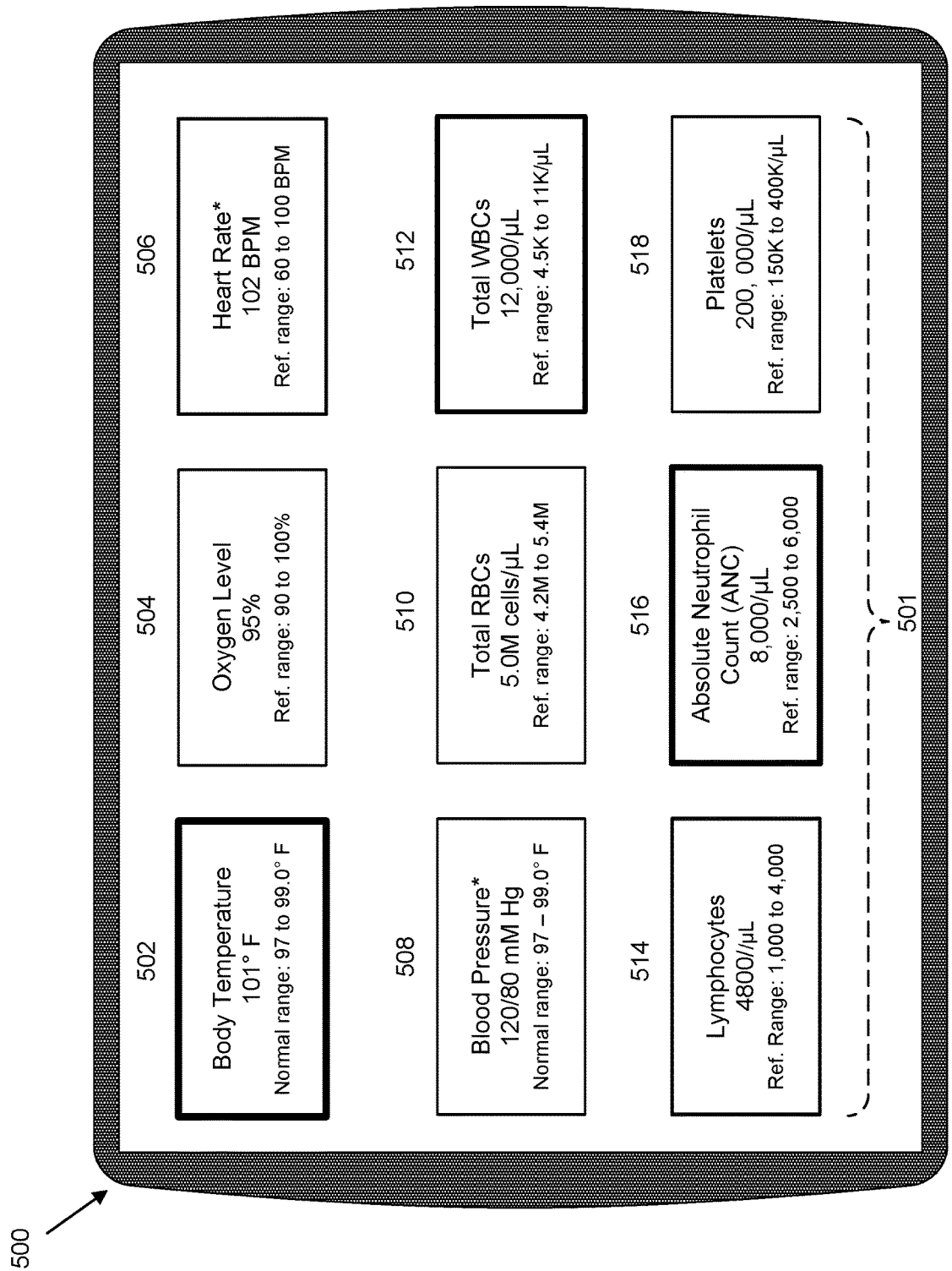
FIG. 5A depicts an example interface for a health care provider of results captured using an implantable venous access port with remote physiological monitoring capabilities.
Figure 5B:
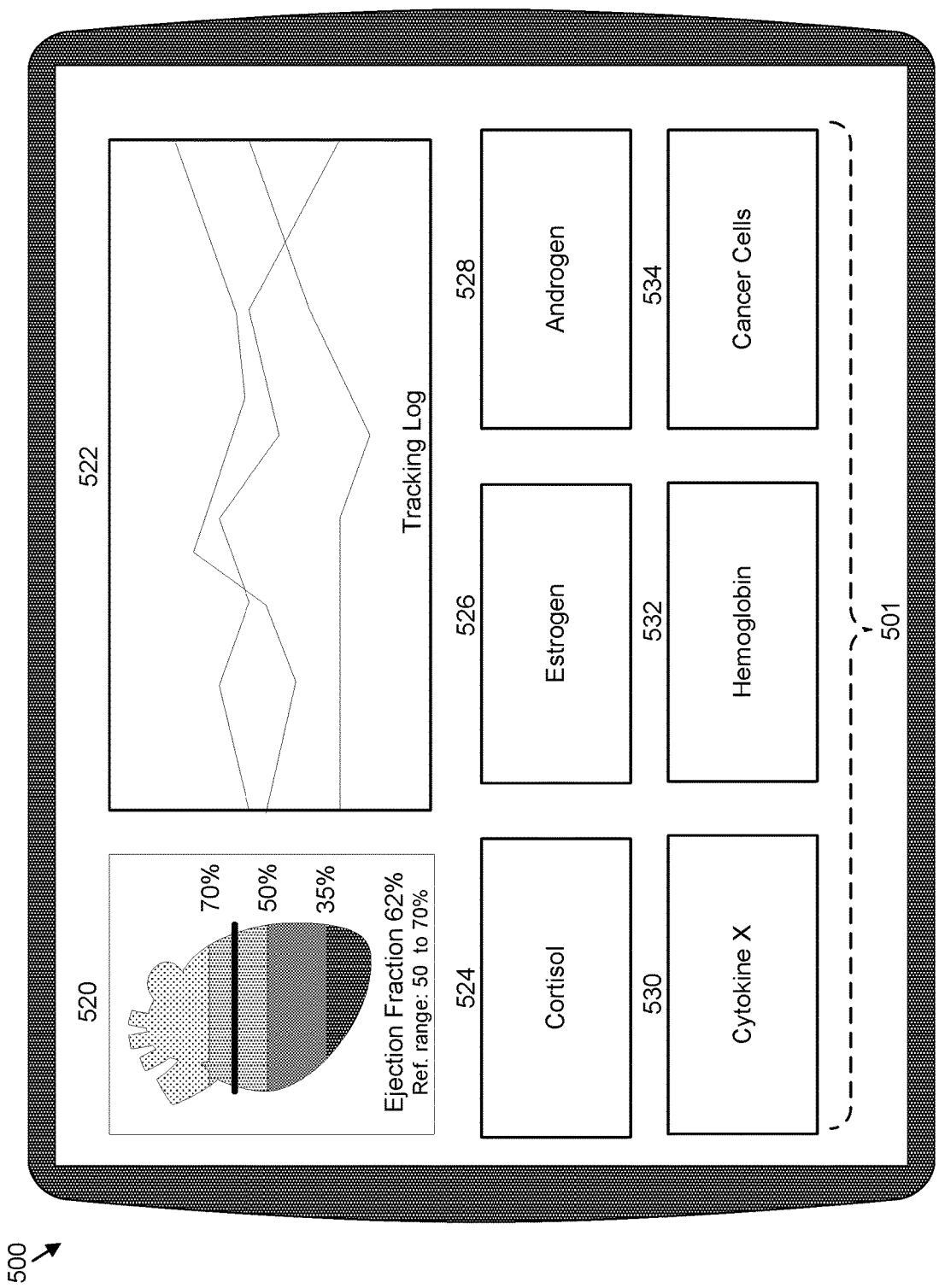
FIG. 5B depicts another example interface for a health care provider of results captured using an implantable venous access port with remote physiological monitoring capabilities.

FIGS. 5A and 5B depict an interface 500 for a health care provider or another authorized user in accordance with one or more embodiments of the present disclosure. The interface 500 may be presented on a display of a mobile device, a laptop device, a desktop device, a wearable device (e.g., a health/fitness monitor worn on the wrist or embedded in another article of clothing), and so forth. The interface may provide various outputs for the healthcare provider to consider based on the sensed data from the sensor microassembly 162 and received from the control module 138.

The interface 500, as shown in FIGS. 5A and 5B, may present data including physiological indicators 501. The physiological indicators 501 may include various parameters such as the patient's body temperature 502, the oxygen level 504, heart rate 506, blood pressure 508, total red blood cell count 510, total white blood cell count 512, lymphocytes 514, absolute neutrophil count 516, platelets 518, ejection fraction 520, a tracking log 522, cortisol 524, estrogen 526, androgen 528, cytokine(s) 530, hemoglobin 532, cancer cells 534, and/or the like. In some embodiments, a user may select one or more of the displayed outputs 502-534 to drill down into more details about those outputs, e.g., averages over time, filtering to a particular time period or type, and/or the like.

Figure 6A:
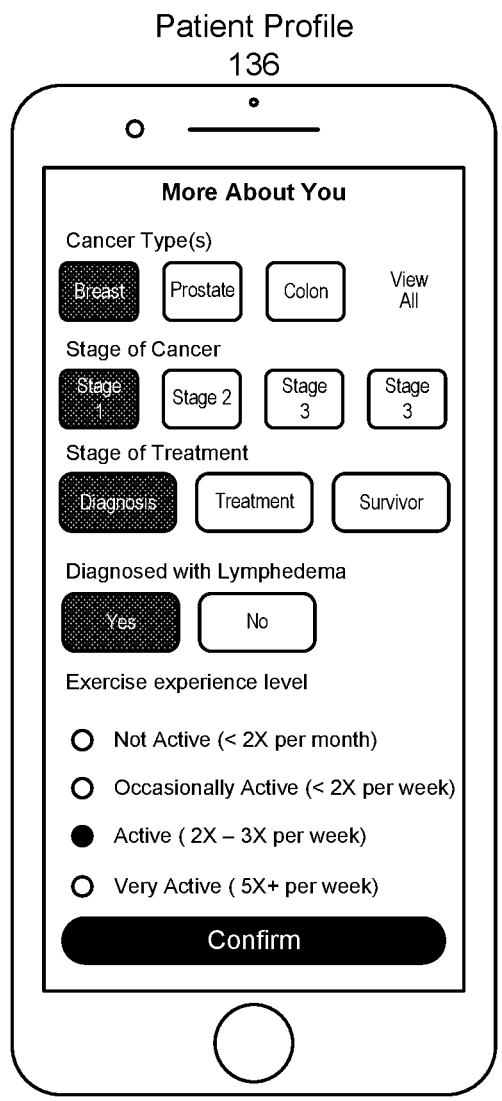
FIG. 6A depicts an example interface for a patient of a profile for an implantable venous access port with remote physiological monitoring capabilities.

FIG. 6A depicts an example interface of a profile 136 of the patient 104. The profile 136 may be presented on a display of a mobile device, a laptop device, a desktop device, and/or the like. The profile 136 may include options for the patient 104 to select so that the outputs, measurements, calculations, and/or the like are relevant to the patient's condition. For example, as shown in FIG. 6A, the patient may be able to specify the type of cancer that he/she has, the stage of the cancer, the state of treatment, whether the patient 104 was diagnosed with lymphedema, the activity level of the patient 104, and/or the like.

Figure 6B:
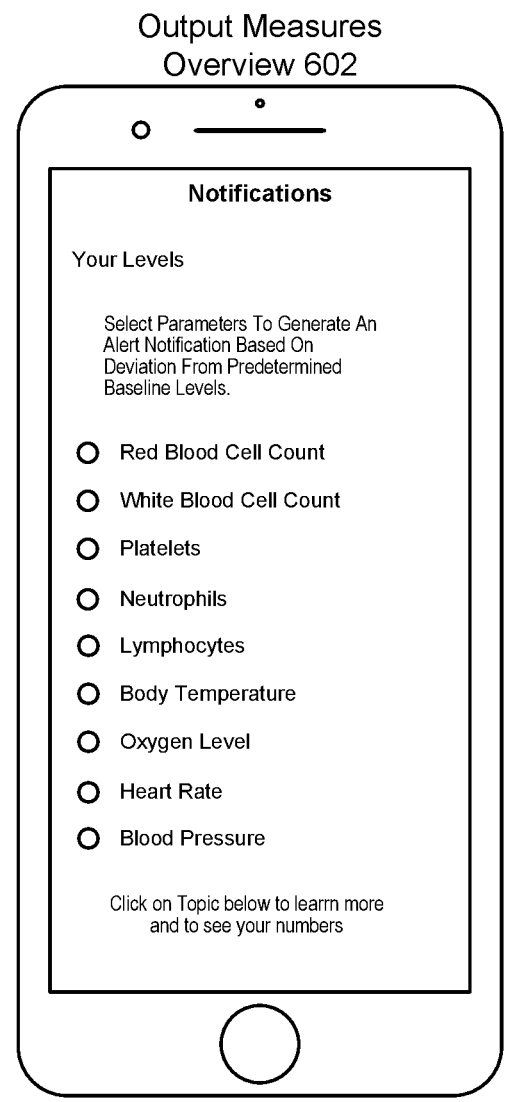
FIG. 6B depicts an example interface for a patient of results captured using an implantable venous access port with remote physiological monitoring capabilities.

FIG. 6B depicts an example interface of the output measures overview 602 for the various measurements based on the data that the sensors of the sensor microassembly 162 detects. The output measures overview 602 may be presented on a display of a mobile device, a laptop device, a desktop device, and/or the like. For example, a patient 104 may be able to drill down into various physiological measurements related to the patient's condition such as the red blood cell count, white blood cell count, platelets, neutrophils, lymphocytes, body temperature, oxygen level, heart rate, blood pressure, and/or the like.

For example, spikes in body temperature or heart rate may indicate the patient is experiencing a side effect of the therapeutic agent or may have an infection. Increases in certain blood cell counts, such as neutrophils or lymphocytes may also indicate the patient is experiencing an infection, in which physician intervention is required. The output measures overview 602 provides an interface by which a patient or another user can select a set of physiological conditions to be utilized as input to the alert module.

Figure 6C:
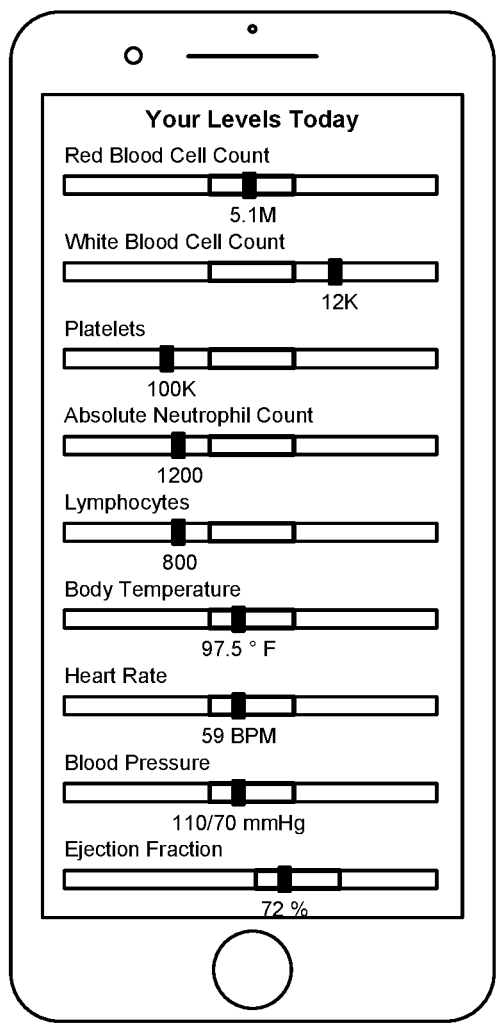
FIG. 6C depicts another example interface for a patient of results captured using an implantable venous access port with remote physiological monitoring capabilities.

FIG. 6C depicts an example interface of the specific levels of the output measures 604 for the various measurements based on the data that the sensors of the sensor microassembly 162 detects. The specific levels of the output measures 604 may be presented on a display of a mobile device, a laptop device, a wearable, a desktop device, and/or the like. The interface may present a visual chart, graph, or the like that shows the patient's current measurement level (or average measurement level over a period of time), and a range that the patient's levels should be in.

Figure 6D:
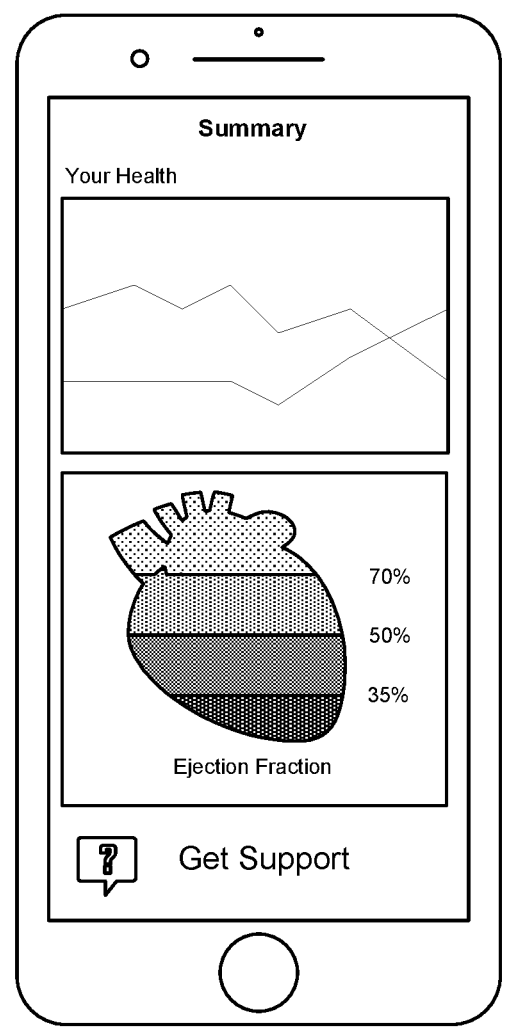
FIG. 6D depicts another example interface for a patient of results captured using an implantable venous access port with remote physiological monitoring capabilities.

FIG. 6D depicts an example interface of the patient support program summary screen. The patient support program summary screen 606 may be presented on a display of a mobile device, a laptop device, a desktop device, and/or the like. In one example embodiment, the patient support program summary screen 606 presents various logs, charts, graphs, plots, or the like of the patient's health measurements, ejection fraction, or the like and/or a link to get more support/help from an authorized user such as a healthcare professional. In various embodiments, the charts, graphs, plots are generated by the plot module as implemented in one or more of the computing devices 106a, 106b depicted in FIG. 1B.

Figure 7:
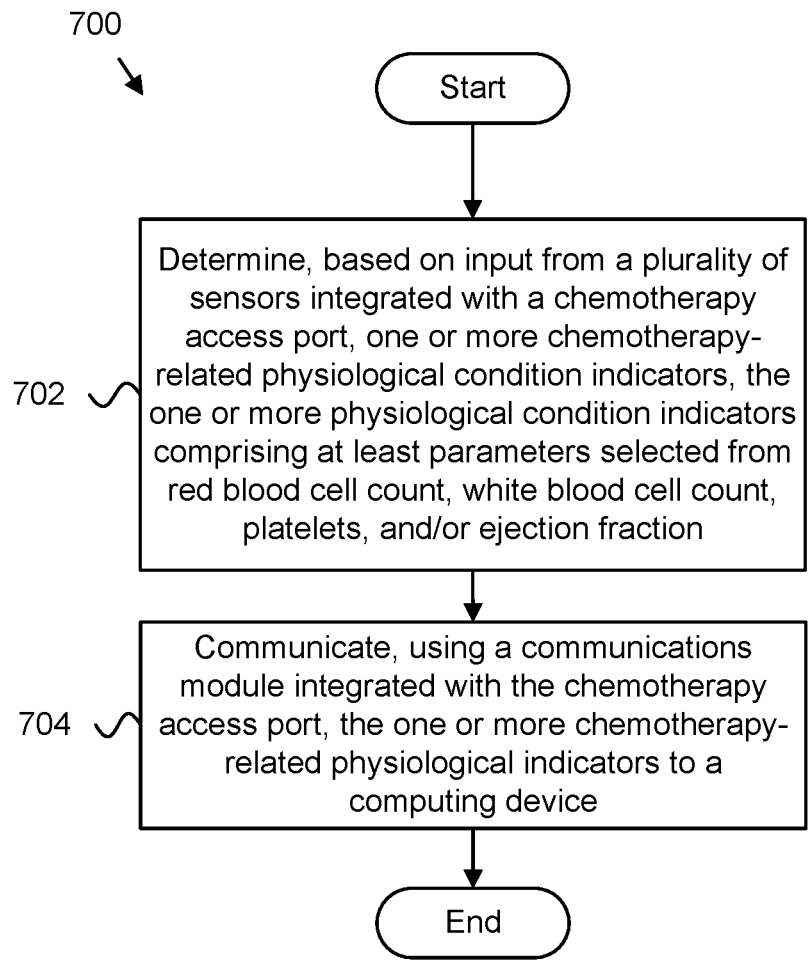
FIG. 7 depicts one embodiment of a schematic flow chart diagram for an implantable venous access port with remote physiological monitoring capabilities.

FIG. 7 is a schematic flow-chart diagram illustrating one embodiment of a method 700 for an implantable venous access port with remote physiological monitoring capabilities. In one embodiment, the method 700 begins and determines 702, based on input from a plurality of sensors integrated with a chemotherapy access port, one or more chemotherapy-related physiological indicators. The one or more physiological indicators may include at least parameters selected from red blood cell count, white blood cell count, platelets, and/or ejection fraction.

In one embodiment, the method 700 communicates 704, using a communications module integrated with the chemotherapy access port, the one or more chemotherapy-related physiological indicators to a corresponding communication module of a computing device, and the method 700 ends.

Figure 8:
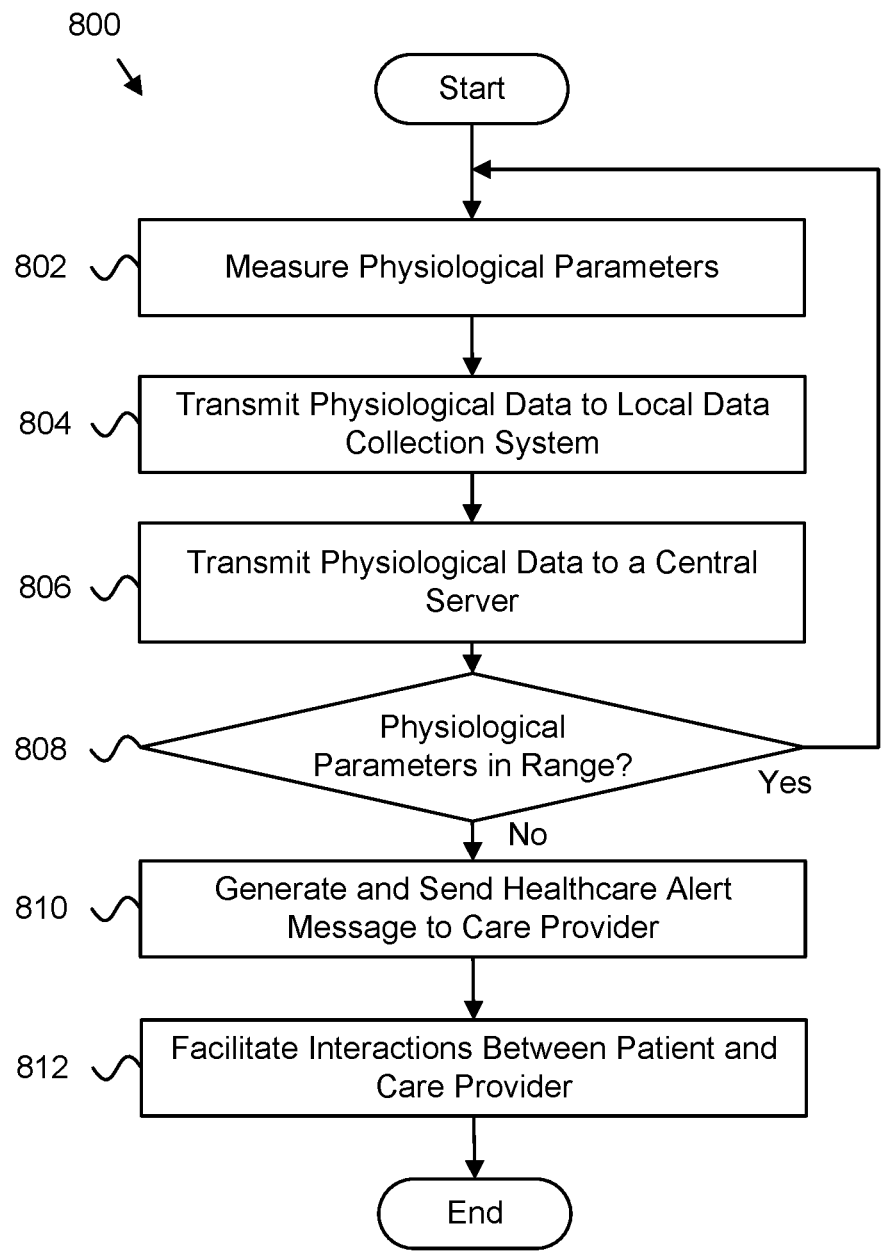
FIG. 8 depicts another embodiment of a schematic flow chart diagram for an implantable venous access port with remote physiological monitoring capabilities.

FIG. 8 is a schematic flow-chart diagram illustrating one embodiment of a method 800 for an implantable venous access port with remote physiological monitoring capabilities. In one embodiment, the method 800 begins and measures 802 one or more chemotherapy-related physiological indicators/parameters using one or more sensors integrated with the IVAP device 102.

In further embodiments, the method 800 transmits 804 the physiological indicators/parameters to a local computing device 106a which may also be referred to as a local data collection system. In some embodiments, the method 800 transmits 806 the physiological indicators/parameters to a central server 110.

In one embodiment, if the method 800 determines 808 that the physiological indicators/parameters are within a predefined/expected range, then the method 800 continues to measure 802 one or more chemotherapy-related physiological indicators/parameters using one or more sensors integrated with the IVAP device 102.

Otherwise, the method 800, in one embodiment, generates and sends 810 healthcare alert messages to an authorized user such as a healthcare provider 116. The method 800, in further embodiments, facilitates 812 interactions between the patient 104 and healthcare provider 116, e.g., via a mobile application as depicted in FIGS. 5A-6D, and the method 800 ends.

The apparatus, system, and methods described in the various embodiments above provide a number of important improvements over existing methods of monitoring physiological conditions of a chemotherapy patient. For example, among the beneficial aspects of the apparatus, system, and methods described in the present disclosure are to monitor physiological functions in an integrated fashion and in real time and earlier evidence of physiological deviations to expected levels. This saves the time for the patient, physician, and laboratory time, as well as reducing overall costs to health care system.

Also among the beneficial aspects are capturing data indicative of physiological trends by monitoring over time.

A physician, and if warranted, a researcher or pharma company, can determine individualized responses to therapy (side effects or drug effectiveness). In the era of personalized medicine, the patient data may be critical to adjusting dosage/therapy and responding to what works best for the individual patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
    a chemotherapy access port;
    a plurality of sensors connected to a sensor interface integrated with the chemotherapy access port, the plurality of sensors configured to determine one or more chemotherapy-related physiological indicators, the one or more physiological indicators comprising at least parameters selected from red blood cell count, white blood cell count, platelets, and/or ejection fraction;
    a communications module integrated with the chemotherapy access port, the communications module configured to communicate the one or more chemotherapy-related physiological indicators to a computing device;
    wherein the plurality of sensors comprises an autofluorescence sensor configured to perform an in-vivo count of red blood cells, white blood cells, and platelets;
    wherein the autofluorescence sensor comprises:
        a source configured to generate and emit excitation light within a predefined light wavelength range;
        a plurality of photosensors configured to detect, record, and quantify autofluorescence emitted by the red blood cells, the white blood cells, and/or the platelets in response to the excitation light, the plurality of photosensor placed at a predefined distance from one another, the predefined distance between at least two photosensors of the plurality of photosensors used to calculate blood flow velocity, ejection time, ejection fraction, and cardiac output.

2. The apparatus of claim 1, wherein the autofluorescence sensor determines whether a cell is a red blood cell, a white blood cell, or a platelet, based on one or more measurements of autofluorescence detected at the plurality of photosensors, the measurements selected from autofluorescence magnitude, autofluorescence wavelength, autofluorescence decay rate, and combinations thereof.

3. The apparatus of claim 1, wherein the plurality of photosensors is arranged in one or more arrays to yield spatially registered optical measurements.

4. The apparatus of claim 3, wherein the one or more arrays of the plurality of photosensors are configured to perform light-scattering measurements for quantifying non-cellular components of blood.

5. The apparatus of claim 4, wherein the non-cellular components of the blood are identified based on spectral dependent optical density measurements, spectral dependent light scattering measurements, and/or spectral dependent autofluorescence intensity and lifetime measurements, and combinations thereof, as registered by at least two arrays of the plurality of photosensors.

6. The apparatus of claim 4, wherein the non-cellular components that are quantified comprise one or more of protein content including albumin, bilirubin, hemoglobin, myoglobin, creatinine, and/or free nucleic acids.

7. The apparatus of claim 1, wherein the predefined light wavelength range of the excitation light is about 280 nm to about 1400 nm.

8. The apparatus of claim 1, wherein the source is tunable to control one or more of an intensity, a frequency, a wavelength, and/or a duration.

9. The apparatus of claim 1, wherein the source comprises one or more light-emitting components selected from a point source light-emitting diode ("LED"), a laser diode, an optical fiber, and combinations thereof.

10. The apparatus of claim 1, further comprising a plot module configured to generate a plot of at least the red blood cell count, the white blood cell count, and the platelet count, over time.

11. The apparatus of claim 1, further comprising an alert module configured to transmit one or more patient health alerts from the chemotherapy access port to an authorized user in response to the one or more chemotherapy-related physiological indicators being outside threshold values.

12. The apparatus of claim 11, wherein the threshold values are determined based on previous measurements of the one or more chemotherapy-related physiological indicators, the previous measurements stored on a memory integrated with the chemotherapy access port.

13. The apparatus of claim 11, wherein the alert module is configured to transmit the one or more patient health alerts in response to the one or more chemotherapy-related physiological indicators being outside the threshold values for a predefined period of time.

14. The apparatus of claim 1, further comprising an encryption module configured to encrypt the one or more chemotherapy-related physiological indicators prior to communicating with the computing device.

15. A method, comprising:
    inserting in the superior vena cava of a subject an autofluorescence sensor that interfaces with an implantable venous access port, the autofluorescence sensor comprising an excitation emitter and at least two photosensors disposed at a predefined distance from one another;
    emitting excitation light within a predefined wavelength range from the excitation emitter;
    quantifying in vivo autofluorescence emitted by red blood cells, white blood cells and/or platelets using the predefined distances and differences in detection time between the at least two photosensors to calculate blood flow velocity, ejection time, ejection fraction, and cardiac output, based on the predefined distances between the at least two photosensors and a difference in time it takes for an autofluorescence signal to be detected by at least two photosensors;
    based on input from a plurality of sensors integrated with a chemotherapy access port, one or more physiological indicators, the one or more physiological indicators comprising at least parameters selected from red blood cell count, white blood cell count, platelets, and/or ejection fraction; and
    communicating, using a communications module integrated with the implantable venous access port, the one or more physiological indicators to a computing device.

16. The method of claim 15, further comprising arranging the plurality of photosensors in one or more arrays to yield spatially registered optical measurements.

17. The method of claim 16, further comprising quantifying non-cellular components of blood by performing light-scattering measurements using the one or more arrays arranged from the plurality of photosensors.

18. The method of claim 17, wherein the quantifying of the non-cellular components of blood comprises quantifying one or more of protein content selected from albumin, bilirubin, hemoglobin, myoglobin, and/or creatinine, and/or quantifying free nucleic acids.

19. A system, comprising:
  a implantable venous access port; and
  a hardware device integrated with the implantable venous access port, the hardware device comprising:
    a processor;
    a memory;
    a power source;
  an autofluorescence sensor communicatively coupled to the implantable venous access port and comprising:
    a source configured to generate and emit excitation light within a predefined light wavelength range; and
    at least two photosensors placed at a predefined distance from one another and configured to detect, record, and quantify autofluorescence emitted by red blood cells, white blood cells, and/or platelets in response to the excitation light to get a red blood cell count, a white blood cell count, a platelet count, and/or ejection fraction information based on calculations of blood flow velocity, ejection time, ejection fraction, and cardiac output, made using the predefined distances between the at least two photosensors and a difference in time it takes for an autofluorescence signal to be detected by at least two photosensors; and
  a communications module integrated with the implantable venous access port and operably coupled to the processor, the communications module configured to communicate the red blood cell count, the white blood cell count, the platelet count, and/or the ejection fraction information to a computing device.

20. The system of claim 19, further comprising a plot module configured to generate a plot of at least the red blood cell count, the white blood cell count, and the platelet count, over time.

* * * * *